United States Patent
Zhang et al.

(10) Patent No.: US 9,339,243 B2
(45) Date of Patent: *May 17, 2016

(54) IMAGE GUIDED RADIOTHERAPY WITH DUAL SOURCE AND DUAL DETECTOR ARRAYS TETRAHEDRON BEAM COMPUTED TOMOGRAPHY

(71) Applicant: William Beaumont Hospital, Royal Oak, MI (US)

(72) Inventors: Tiezhi Zhang, St. Louis, MO (US); Joshua Kim, Royal Oak, MI (US)

(73) Assignee: WILLIAM BEAUMONT HOSPITAL, Royal Oak, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/275,794

(22) Filed: May 12, 2014

(65) Prior Publication Data

US 2014/0247919 A1    Sep. 4, 2014

Related U.S. Application Data

(63) Continuation-in-part of application No. 13/194,215, filed on Jul. 29, 2011, now Pat. No. 8,983,024, which is a continuation-in-part of application No. 12/803,480, filed on Jun. 29, 2010, now Pat. No.

(Continued)

(51) Int. Cl.
*A61B 6/03*    (2006.01)
*A61B 6/02*    (2006.01)
(Continued)

(52) U.S. Cl.
CPC ............... *A61B 6/032* (2013.01); *A61B 6/022* (2013.01); *A61B 6/025* (2013.01); *A61B 6/06* (2013.01);
(Continued)

(58) Field of Classification Search
CPC ........ A61B 6/032; A61B 6/025; A61B 6/027; A61B 6/06; A61B 6/4007; A61B 6/4028; A61B 6/4064; A61B 6/4266; A61B 6/4441; A61B 6/4488; A61B 6/466; A61N 2005/1061; A61N 5/1049; A61N 5/1067; G21K 1/02; G21K 1/025; H01J 2235/062

See application file for complete search history.

(56) References Cited

U.S. PATENT DOCUMENTS

| | | | |
|---|---|---|---|
| 3,778,614 | A | 12/1973 | Hounsfield |
| 3,780,291 | A | 12/1973 | Stein et al. |

(Continued)

FOREIGN PATENT DOCUMENTS

| | | |
|---|---|---|
| CN | 1419891A A1 | 5/2003 |
| CN | 1424925 A | 6/2003 |

(Continued)

OTHER PUBLICATIONS

Antonuk, L.E., et al., "A Real-Time, Flat-Panel, Amorphous Silicon, Digital X-Ray Imager", Radiographics, vol. 15, No. 4, Jul. 1995, pp. 993-1000.

(Continued)

*Primary Examiner* — Glen Kao
(74) *Attorney, Agent, or Firm* — Armstrong Teasdale LLP

(57) ABSTRACT

A radiation treatment and imaging system for emitting a radiation treatment beam and X-ray imaging beams towards an object. The system includes an x-ray source and a collimator, first and second detectors, and a linear accelerator that delivers radiation beams to an object. The linear accelerator includes a radiation source positioned between the first and second detectors and emitting a therapy radiation beam in-line with the x-ray beams received by the first and second detectors. The system also includes a data processing device in communication with the first and second detectors. The data processing device receives imaging signals from the first and second detectors and reconstructs a three-dimensional tetrahedron beam computed tomography (TBCT) image from the received imaging signals. The system also includes a display in communication with the data processing device and for displaying the TBCT image.

23 Claims, 23 Drawing Sheets

Related U.S. Application Data 8,611,490, which is a continuation of application No. 11/786,781, filed on Apr. 12, 2007, now Pat. No. 7,760,849.

(60) Provisional application No. 61/822,036, filed on May 10, 2013, provisional application No. 60/792,207, filed on Apr. 14, 2006.

(51) Int. Cl.
  *A61N 5/10* (2006.01)
  *A61B 6/06* (2006.01)
  *A61B 6/00* (2006.01)
  *G21K 1/02* (2006.01)
  *H05G 1/70* (2006.01)

(52) U.S. Cl.
  CPC ............ *A61B 6/4007* (2013.01); *A61B 6/4028* (2013.01); *A61B 6/4064* (2013.01); *A61B 6/4266* (2013.01); *A61B 6/466* (2013.01); *A61N 5/1049* (2013.01); *A61N 5/1067* (2013.01); *G21K 1/025* (2013.01); *A61B 6/027* (2013.01); *A61B 6/4441* (2013.01); *A61B 6/4488* (2013.01); *A61N 2005/1061* (2013.01); *G21K 1/02* (2013.01); *H01J 2235/062* (2013.01); *H01J 2235/068* (2013.01); *H05G 1/70* (2013.01)

(56) References Cited

U.S. PATENT DOCUMENTS

| | | | |
|---|---|---|---|
| 4,132,895 A | 1/1979 | Froggatt | |
| 4,145,613 A | 3/1979 | Bunch | |
| 4,304,999 A | 12/1981 | Richey et al. | |
| 4,315,157 A | 2/1982 | Barnes | |
| 4,380,818 A | 4/1983 | Pfeiler | |
| 4,389,569 A | 6/1983 | Hattori et al. | |
| 4,405,745 A | 9/1983 | Mathis et al. | |
| 4,414,682 A | 11/1983 | Annis et al. | |
| 4,534,051 A | 8/1985 | Grady et al. | |
| 4,547,892 A | 10/1985 | Richey et al. | |
| 4,712,226 A | 12/1987 | Horbaschek | |
| 4,920,552 A | 4/1990 | Hermens | |
| 5,039,867 A | 8/1991 | Nishihara et al. | |
| 5,125,012 A | 6/1992 | Schittenhelm | |
| 5,157,707 A | 10/1992 | Ohlson | |
| 5,214,686 A | 5/1993 | Webber | |
| 5,335,255 A | 8/1994 | Seppi et al. | |
| 5,359,639 A | 10/1994 | Saito | |
| 5,379,333 A | 1/1995 | Toth | |
| 5,394,452 A | 2/1995 | Swerdloff et al. | |
| 5,411,026 A | 5/1995 | Carol | |
| 5,438,991 A | 8/1995 | Yu et al. | |
| 5,485,494 A | 1/1996 | Williams et al. | |
| 5,521,957 A | 5/1996 | Hansen | |
| 5,533,082 A | 7/1996 | Gronemeyer et al. | |
| 5,602,892 A | 2/1997 | Llacer | |
| 5,625,661 A | 4/1997 | Oikawa | |
| 5,657,364 A | 8/1997 | Pfoh | |
| 5,661,773 A | 8/1997 | Swerdloff et al. | |
| 5,663,995 A | 9/1997 | Hu | |
| 5,675,625 A | 10/1997 | Rockseisen | |
| 5,699,805 A | 12/1997 | Seward et al. | |
| 5,719,914 A | 2/1998 | Rand et al. | |
| 5,724,400 A | 3/1998 | Swerdloff et al. | |
| 5,748,700 A | 5/1998 | Shepherd et al. | |
| 5,751,781 A | 5/1998 | Brown et al. | |
| 5,835,558 A | 11/1998 | Maschke | |
| 5,848,126 A | 12/1998 | Fujita et al. | |
| 5,864,597 A | 1/1999 | Kobayashi | |
| 5,877,501 A | 3/1999 | Ivan et al. | |
| 5,912,943 A | 6/1999 | Deucher et al. | |
| 5,929,449 A | 7/1999 | Huang | |
| 5,949,811 A | 9/1999 | Baba et al. | |
| 5,966,422 A | 10/1999 | Dafni et al. | |
| 5,999,587 A | 12/1999 | Ning et al. | |
| 6,031,888 A | 2/2000 | Ivan et al. | |
| 6,041,097 A | 3/2000 | Roos et al. | |
| 6,113,264 A | 9/2000 | Watanabe | |
| 6,148,058 A | 11/2000 | Dobbs | |
| 6,152,598 A | 11/2000 | Tomisaki et al. | |
| 6,200,024 B1 | 3/2001 | Negrelli | |
| 6,229,870 B1 | 5/2001 | Morgan | |
| 6,239,439 B1 | 5/2001 | Itabashi et al. | |
| 6,256,370 B1 | 7/2001 | Yavuz | |
| 6,259,766 B1 | 7/2001 | Cuppen | |
| 6,269,143 B1 | 7/2001 | Tachibana | |
| 6,285,739 B1 | 9/2001 | Rudin et al. | |
| 6,292,534 B1 | 9/2001 | Linders et al. | |
| 6,298,115 B1 * | 10/2001 | Nilsson ..................... 378/65 |
| 6,307,914 B1 | 10/2001 | Kunieda et al. | |
| 6,318,892 B1 | 11/2001 | Suzuki et al. | |
| 6,325,537 B1 | 12/2001 | Watanabe | |
| 6,325,758 B1 | 12/2001 | Carol et al. | |
| 6,345,114 B1 | 2/2002 | MacKie et al. | |
| 6,385,286 B1 | 5/2002 | Fitchard et al. | |
| 6,385,288 B1 | 5/2002 | Kanematsu | |
| 6,389,104 B1 | 5/2002 | Bani-Hashemi et al. | |
| 6,393,096 B1 | 5/2002 | Carol et al. | |
| 6,435,715 B1 | 8/2002 | Betz et al. | |
| 6,463,122 B1 | 10/2002 | Moore | |
| 6,546,073 B1 | 4/2003 | Lee | |
| 6,560,311 B1 | 5/2003 | Shepart et al. | |
| 6,582,121 B2 | 6/2003 | Crain et al. | |
| 6,618,466 B1 | 9/2003 | Ning | |
| 6,628,745 B1 | 9/2003 | Annis et al. | |
| 6,633,627 B2 | 10/2003 | Horiuchi | |
| 6,661,870 B2 | 12/2003 | Kapatoes et al. | |
| 6,707,876 B2 | 3/2004 | Tanigawa | |
| 6,760,402 B2 | 7/2004 | Ghelmansarai | |
| 6,792,074 B2 | 9/2004 | Erbel et al. | |
| 6,810,107 B2 | 10/2004 | Steinberg | |
| 6,842,502 B2 | 1/2005 | Jaffray et al. | |
| 6,865,254 B2 | 3/2005 | Nafstadius | |
| 6,888,919 B2 | 5/2005 | Graf | |
| 6,907,100 B2 | 6/2005 | Taguchi | |
| 6,915,005 B1 | 7/2005 | Ruchala et al. | |
| 6,980,627 B2 | 12/2005 | Qiu et al. | |
| 6,990,175 B2 | 1/2006 | Nakashima et al. | |
| 6,993,112 B2 | 1/2006 | Hesse | |
| 7,030,386 B2 | 4/2006 | Pang et al. | |
| 7,054,801 B2 | 5/2006 | Sakamoto et al. | |
| 7,062,006 B1 | 6/2006 | Pelc et al. | |
| 7,072,436 B2 | 7/2006 | Pelc | |
| 7,110,808 B2 | 9/2006 | Adair | |
| 7,127,035 B2 | 10/2006 | Anno et al. | |
| 7,145,981 B2 | 12/2006 | Pelc | |
| 7,154,991 B2 | 12/2006 | Earnst et al. | |
| 7,170,975 B2 | 1/2007 | Distler et al. | |
| 7,193,227 B2 | 3/2007 | Hiramoto et al. | |
| 7,227,923 B2 | 6/2007 | Edic et al. | |
| 7,227,925 B1 | 6/2007 | Mansfield et al. | |
| 7,280,631 B2 | 10/2007 | De Man et al. | |
| 7,305,063 B2 | 12/2007 | Heuscher | |
| 7,388,940 B1 | 6/2008 | De Man et al. | |
| 7,428,292 B2 | 9/2008 | Deman et al. | |
| 7,471,765 B2 | 12/2008 | Jaffray et al. | |
| 7,496,181 B2 | 2/2009 | Mazin et al. | |
| 7,657,304 B2 | 2/2010 | Mansfield et al. | |
| 7,760,849 B2 | 7/2010 | Zhang | |
| 7,826,592 B2 | 11/2010 | Jaffray et al. | |
| 7,945,021 B2 | 5/2011 | Shapiro et al. | |
| 8,073,105 B2 | 12/2011 | Gertner et al. | |
| 8,983,024 B2 * | 3/2015 | Zhang et al. ................ 378/4 |
| 2003/0072425 A1 | 4/2003 | Mihara et al. | |
| 2003/0095627 A1 | 5/2003 | Anderton | |
| 2003/0138077 A1 | 7/2003 | Lee | |
| 2003/0191363 A1 | 10/2003 | Boll et al. | |
| 2003/0235271 A1 | 12/2003 | Rand | |
| 2004/0002641 A1 | 1/2004 | Sjogren et al. | |
| 2004/0042583 A1 * | 3/2004 | Wackerle et al. ........... 378/65 |
| 2004/0081270 A1 | 4/2004 | Heuscher | |

(56) References Cited

U.S. PATENT DOCUMENTS

| | | |
|---|---|---|
| 2004/0086074 A1 | 5/2004 | Taguchi |
| 2004/0096033 A1 | 5/2004 | Seppi et al. |
| 2004/0120452 A1 | 6/2004 | Shapiro et al. |
| 2004/0165696 A1 | 8/2004 | Lee |
| 2004/0174949 A1 | 9/2004 | Yamashita et al. |
| 2004/0184578 A1 | 9/2004 | Nakano |
| 2004/0254448 A1 | 12/2004 | Amies et al. |
| 2005/0013404 A1 | 1/2005 | Kasperl et al. |
| 2005/0027196 A1 | 2/2005 | Fitzgerald |
| 2005/0053189 A1 | 3/2005 | Gohno et al. |
| 2005/0054937 A1 | 3/2005 | Takaoka et al. |
| 2005/0058237 A1 | 3/2005 | Morf |
| 2005/0080336 A1 | 4/2005 | Byrd et al. |
| 2005/0085710 A1 | 4/2005 | Earnst et al. |
| 2005/0111610 A1 | 5/2005 | Deman et al. |
| 2005/0111616 A1 | 5/2005 | Li et al. |
| 2005/0111621 A1 | 5/2005 | Riker et al. |
| 2005/0197564 A1 | 9/2005 | Dempsey |
| 2005/0234327 A1 | 10/2005 | Saracen et al. |
| 2005/0249432 A1 | 11/2005 | Zou et al. |
| 2005/0251029 A1 | 11/2005 | Khamene et al. |
| 2006/0002506 A1 | 1/2006 | Pelc |
| 2006/0008047 A1 | 1/2006 | Zhou et al. |
| 2006/0017009 A1 | 1/2006 | Rink et al. |
| 2006/0067468 A1* | 3/2006 | Rietzel ............... A61N 5/1049 378/65 |
| 2006/0239409 A1 | 10/2006 | Levene et al. |
| 2006/0245543 A1 | 11/2006 | Earnst et al. |
| 2006/0259282 A1 | 11/2006 | Failla et al. |
| 2006/0269049 A1 | 11/2006 | Yin et al. |
| 2006/0274885 A1 | 12/2006 | Wang et al. |
| 2006/0285639 A1 | 12/2006 | Olivera et al. |
| 2006/0285640 A1 | 12/2006 | Nizin et al. |
| 2006/0285641 A1 | 12/2006 | Scherch |
| 2007/0003123 A1 | 1/2007 | Fu et al. |
| 2007/0016014 A1 | 1/2007 | Hara et al. |
| 2007/0019782 A1 | 1/2007 | Van Stevendaal et al. |
| 2007/0053492 A1 | 3/2007 | Kidani et al. |
| 2007/0076846 A1 | 4/2007 | Ruchala et al. |
| 2007/0230660 A1 | 10/2007 | Herrmann |
| 2007/0280408 A1 | 12/2007 | Zhang |
| 2008/0031406 A1 | 2/2008 | Yan et al. |
| 2010/0008467 A1 | 1/2010 | Dussault et al. |
| 2010/0054410 A1 | 3/2010 | Nord et al. |
| 2010/0119032 A1 | 5/2010 | Yan et al. |
| 2010/0135454 A1 | 6/2010 | Noo |
| 2011/0002439 A1 | 1/2011 | Zhang |
| 2011/0080992 A1 | 4/2011 | Dafni |
| 2011/0211665 A1* | 9/2011 | Maurer, Jr. ............... A61N 5/10 378/9 |
| 2011/0211666 A1 | 9/2011 | Ying et al. |
| 2013/0142310 A1 | 6/2013 | Fahimlan et al. |

FOREIGN PATENT DOCUMENTS

| | | |
|---|---|---|
| CN | 1589744 A | 3/2005 |
| CN | 1723743 A | 1/2006 |
| CN | 1748217A A1 | 3/2006 |
| CN | 1758876A A1 | 4/2006 |
| DE | 1992708 U | 8/1968 |
| DE | 2822241 A1 | 12/1978 |
| EP | 0314231 A2 | 5/1989 |
| EP | 0922943 A2 | 6/1999 |
| JP | 5252594 A | 4/1977 |
| JP | 56101579 A | 8/1981 |
| JP | 56168578 A | 12/1981 |
| JP | 5894835 A | 6/1983 |
| JP | 58163341 | 9/1983 |
| JP | 4242736 A | 8/1992 |
| JP | 04307035 | 10/1992 |
| JP | 5172764 A | 7/1993 |
| JP | 06506860 | 8/1994 |
| JP | 07255717 A | 10/1995 |
| JP | 08122438 A | 5/1996 |
| JP | 09-218939 A | 8/1997 |
| JP | 09327453 A | 12/1997 |
| JP | 10-033520 A | 2/1998 |
| JP | 10113400 A | 5/1998 |
| JP | 10295683 A | 11/1998 |
| JP | 10511595 A | 11/1998 |
| JP | 10328318 A | 12/1998 |
| JP | 11047290 A | 2/1999 |
| JP | 1199148 A | 4/1999 |
| JP | 11160440 A | 6/1999 |
| JP | 11-276463 | 10/1999 |
| JP | 2000-23968 A | 1/2000 |
| JP | 2000126164 A | 5/2000 |
| JP | 2000176029 A | 6/2000 |
| JP | 2000308634 A | 11/2000 |
| WO | WO97/13552 A1 | 4/1997 |
| WO | WO98/52635 | 11/1998 |
| WO | WO99/03397 | 1/1999 |
| WO | WO0160236 A2 | 8/2001 |
| WO | WO2004061744 A2 | 7/2004 |
| WO | WO2004061864 A2 | 7/2004 |
| WO | WO2004080309 A2 | 9/2004 |
| WO | WO2006/018761 A1 | 2/2006 |

OTHER PUBLICATIONS

Antonuk, L.E., et al., "Initial Performance Evaluation of an Indirect-Detection, Active Matrix Flat-Panel Imager (AMFPI) Prototype for Megavoltage Imaging", Int. J. Radiat. Oncol. Biol. Phys., vol. 42, No. 2, 1998, pp. 437-454.

Antonuk, L.E., et al., "Megavoltage Imaging with a Large-Area, Flat-Panel, Amorphous Silicon Imager", Int. J. Radiat. Oncol. Biol. Phys., vol. 36, No. 3, 1996, pp. 661-672.

Antonuk, L.E., et al., "Strategies to Improve the Signal and Noise Performance of Active Matrix, Flat-Panel Imagers for Diagnostic X-Ray Applications", Med. Phys., vol. 27, No. 2, Feb. 2000, pp. 289-306.

Basset, P.G., Wong, J.W. and Aspin, N.: "An Interactive Computer System for Studying Human Mucociliary Clearance", Computer Biol. Med. 1979, vol. 9, pp. 97-105.

Birkner, M., et al., "Adapting Inverse Planning to Patient and Organ Geometrical Variation: Algorithm and Implementation," Med. Phys., vol. 30, No. 10, Oct. 2003, pp. 2822-2831.

Bissonnette, J.P., et al., "Optimal Radiographic Magnification for Portal Imaging.", Med. Phys., vol. 21, No. 9, Sep. 1994, pp. 1435-1445.

Boyer, A.L., et al., "A Review of Electronic Portal Imaging Devices (EPIDs)", Medical Physics, Jan./Feb. 1992, vol. 19, No. 1, pp. 19: 1-16.

Boyer, A.L., et al., (IMRT Collaborative Working Group): "Intensity-modulated radiotherapy: Current status and issues of interest", Int. J. Radiat. Oncol. Biol. Phys. 2001, vol. 51, No. 4, pp. 880-914.

Brown, A.P. et al., "Three-Dimensional Photon Treatment Planning for Hodgkin's Disease", Int. J. Radiat. Oncol. Biol. Phys., May 15, 1991, vol. 21, No. 1, pp. 205-215.

Chen, J., et al., "Dose-Guided Radiation Therapy with Megavoltage Cone-Beam CT," published by The British Journal of Radiology, vol. 79, 2006, pp. S87-S98.

Cheng, A., et al., "Systematic Verification of a Three-Dimensional Electron Beam Dose Calculation Algorithm", Med. Phys., 1996, vol. 23, No. 5, pp. 685-693.

Chi, Y., et al., "A Material Sensitivity Study on the Accuracy of Deformable Organ Registration Using Linear Biomechanical Models," Med. Phys., vol. 33: No. 2, Feb. 2006, pp. 421-433.

Cullity, B.D., "Elements of X-Ray Diffraction, Second Edition," (Reading, MA: Addison Wesley, 1978), p. 6-12.

Dieu, L., et al., "Ion Beam Sputter-Deposited SiN/TiN Attenuating Phase-Shift Photoblanks," publication source and date unknown, 8 pages.

Drake, D.G., et al., "Characterization of Fluoroscopic Imaging System for kV and MV Radiography", Med. Phys., May 2000, vol. 27, No. 5, pp. 898-905.

Du, M.N., et al., "A Multileaf Collimator Field Prescription Preparation System for Conventional Radiotherapy", Int. J. Radiat. Oncol. Biol. Phys., 1994, vol. 30, No. 3, pp. 707-714.

(56) References Cited

OTHER PUBLICATIONS

Du, M.N., et al., "A Multileaf Collimator Field Prescription Preparation System for Conventional Radiotherapy", Int. J. Radiat. Oncol. Biol. Phys., 1995, vol. 32, No. 2, pp. 513-520.

El-Mohri, Y., et al., "Relative Dosimetry Using Active Matrix Flat-Panel Imager (AMFPI) Technology", Med. Phys., Aug. 1999, vol. 26, No. 8, pp. 1530-1541.

European Search Report for Application No. 07755309.7, dated Apr. 15, 2011, ten pages.

Ezz, A., et al., "Daily Monitoring and Correction of Radiation Field Placement Using a Video-Based Portal Imaging System: a Pilot Study", Int. J. Radiat. Oncol. Biol. Phys., 1992, vol. 22, No. 1, pp. 159-165.

Frazier, A., et al., "Dosimetric Evaluation of the Conformation of the Multileaf Collimator to Irregularly Shaped Fields", Int. J. Radiat. Oncol.Biol. Phys., 1995, vol. 33, No. 5, pp. 1229-1238.

Frazier, A., et al., "Effects of Treatment Setup Variation on Beam's Eye View Dosimetry for Radiation Therapy Using the Multileaf Collimator vs. the Cerrobend Block", Int. J. Radiat. Oncol. Biol. Phys., 1995, vol. 33, No. 5, pp. 1247-1256.

Ghilezan, M., et al., "Online Image-Guided Intensity-Modulated Radiotherapy for Prostate Cancer. How Much Improvement Can We Expect? A Theoretical Assessment of Clinical Benefits and Potential Dose Escalation by Improving Precision and Accuracy of Radiation Delivery," Int. J. Radiation Oncology Biol. Phys., vol. 60, No. 5, 2004, pp. 1602-1610.

Graham, M.L., et al., "A Method to Analyze 2-Dimensional Daily Radiotherapy Portal Images from an On-Line Fiber-Optic Imaging System.", Int. J. Radiat. Oncol. Biol. Phys., Mar. 1991, vol. 20, No. 3, pp. 613-619.

Gupta, N. K., et al., "Tangential CT, A Computed Tomography Method Developed for Industrial Inspection," 16th WCNDT 2004, Sep. 2004, five pages.

Halverson, K.J., et al., "Study of Treatment Variation in the Radiotherapy of Head and Neck Tumors Using a Fiber-Optic On-Line Line Radiotherapy Imaging System", Int. J. Radiat. Oncol. Biol. Phys., Oct. 1991, vol. 21, No. 5, pp. 1327-1336.

Harms, W.B., Sr., et al., "A Software Tool for the Quantitative Evaluation of 3D Dose Calculation Algorithms", Med. Phys., Oct. 1998, vol. 25, No. 10, pp. 1830-1839.

Herman, M.G., et al. "Clinical use of electronic portal imaging: Report of AAPM Radiation Therapy Committee Task Group 58", Med. Phys. May 2001, vol. 28, No. 5, pp. 712-737.

Jaffray, D.A., et al., "A Radiographic and Tomographic Imaging System Integrated into a Medical Linear Accelerator for Localization of Bone and Soft-Tissue Targets", Int. J. Radiat. Oncol. Biol. Phys., 1999, vol. 45, No. 3, pp. 773-789.

Jaffray, D.A., et al., "Activity Distribution of a Cobalt-60 Teletherapy Source", Med. Phys., Mar./Apr. 1991, vol. 18, No. 2, pp. 288-291.

Jaffray, D.A., et al, "Cone-Beam Computed Tomography with a Flat-Panel Imager: Initial Performance Characterization", Med. Phys. Jun. 2000, vol. 27, No. 6, pp. 1311-1323.

Jaffray, D.A., et al., "Dual-Beam Imaging for Online Verification of Radiotherapy Field Placement", Int. J. Radiat. Oncol. Biol. Phys., 1995, vol. 33, No. 5, pp. 1273-1280.

Jaffray, D.A., et al., "X-Ray Scatter in Megavoltage Transmission Radiography: Physical Characteristics and Influence on Image Quality", Med. Phys., Jan. 1994, vol. 21, No. 1, pp. 45-60.

Jaffray, D.A., et al., "X-Ray Sources of Medical Linear Accelerators: Focal and Extra-Focal Radiation", Med. Phys. Sep./Oct. 1993, vol. 20, No. 5, pp. 1417-1427.

Jaffray, et al., "Cone-Beam Computed Tomography with a Flat-Panel Imager: Initial Performance Characterization," Submission to the Medical Physics Journal for publication on Aug. 1999, 36 pages.

Jaffray, et al., Cone-Beam CT: Applications in Image-Guided External Beam Radiotherapy and Brachytherapy, publication source unknown, date unknown, one page.

Jaffray, et al., "Conebeam Tomographic Guidance of Radiation Field Placement for Radiotherapy of the Prostate," Manuscript accepted for publication in the International Journal of Radiation Oncology, Biology, Oct. 1998, 32 pages.

Jaffray, et al., "Exploring 'Target of the Day' Strategies for a Medical Linear Accelerator with Conebeam—CT Scanning Capability," XIIth ICCR held in Salt Lake City, Utah, May 27-30, 1997, pp. 172-174.

Jaffray, et al., "Flat-Panel Cone-Beam CT for Image-Guided External Beam Radiotherapy," publication source unknown, Oct. 1999, 36 pages.

Jaffray, et al., "Managing Geometric Uncertainty in Conformal Intensity-Modulated Radiation Therapy," Seminars in Radiation Oncology, vol. 9, No. 1, Jan. 1999 pp. 4-19.

Jaffray, et al., "Performance of a Volumetric CT Scanner Based Upon a Flat-Panel Imager," SPIE Physics of Medical Imaging, vol. 3659, Feb. 1999, pp. 204-214.

Kapatoes, J.M., et al., "On the Accuracy and Effectiveness of Dose Reconstruction for Tomotherapy," Phys. Med. Biol., vol. 46, 2001, pp. 943-966.

Kessler, M.L., "Image Registration and Data Fusion in Radiation Therapy," The British Journal of Radiology, vol. 79, 2006, pp. S99-S108.

Kestin, L.L., et al., "Improving the Dosimetric Coverage of Interstitial High-Dose-Rate Breast Implants", Int. J. Radial. Oncol. Biol. Phys., 2000, vol. 46, No. 1, pp. 35-43.

Kestin, L.L. et al., "Intensity Modulation to Improve Dose Uniformity with Tangential Breast Radiotherapy: Initial Clinical Experience" Int J. Radiat. Oncol. Biol. Phys., 2000, vol. 48, No. 5, pp. 1559-1568.

Kini, V.R., et al., "Use of Three-Dimensional Radiation Therapy Planning Tools and Intraoperative Ultrasound to Evaluate High Dose Rate Prostate Brachytherapy Implants", Int. J. Radiat. Oncol. Biol. Phys., 1999, vol. 43, No. 3, pp. 571-578.

Kress, J., et al. "Patient position verification using CT images" Medical Physics, AIP, 26(6) 1999, 941-948.

Laughlin, J.S., et al., (Writing chairs), "Evaluation of High Energy Photon External Beam Treatment Planning: Project Summary", Int. J. Rad. Oncol. Biol. Physics. 1991, vol. 21, pp. 3-8.

Liang, J., et al., "Reducing Uncertainties in Volumetric Image Based Deformable Organ Registration," Med. Phys., vol. 30, No. 8, Aug. 2003, pp. 2116-2122.

Moran, Jean M., et al., "Accelerated partial breast irradiation: what is dosimetric effect of advanced technology approaches?," Int. J. Radiat. Oncol. Biol. Phys., vol. 75, No. 1, 2009, pp. 294-301.

Wernicke, A.G., et al., "External beam partial breast irradiation following breast-conserving surgery: preliminary results of cosmetic outcome of NYU 00-23," Int. J. Radiat. Oncol. Biol. Phys. vol. 66, No. 3, Supplement, 2006, p. S32.

Formenti, S. C., et al., "Prone accelerated partial breast irradiation after breast-conserving surgery: preliminary clinical results and dose-volume histogram analysis," Int. J. Radiat. Oncol. Biol. Phys., vol. 60, No. 2, 2004, pp. 493-504.

Kozak, K.R., et al., "Dosimetric comparison of proton and photon three-dimensional, conformal, external beam accelerated partial breast irradiation techniques," Int. J. Radiat. Oncol. Biol. Phys., vol. 65, No. 5, 2006, pp. 1572-1578.

Yu C.X., "Intensity-modulated arc therapy with dynamic multileaf collimation: an alternative to tomotherapy," Phys. Med. Biol., vol. 40, 1995, pp. 1435-1449.

Yu, Cedric X., et al., "Clinical implementation of intensity-modulated arc therapy," Int. J. Radiat. Oncol. Biol. Phys.. vol. 53, No. 2, 2002, pp. 453-463.

Otto K., "Volumetric modulated arc therapy: IMRT in a single gantry arc," Med. Phys., vol. 35, 2008, pp. 310-317.

Palma, D., et al., "Volumetric modulated arc therapy for delivery of prostate radiotherapy: comparison with intensity-modulated radiotherapy and three-dimensional conformal radiotherapy," Int. J. Radiat. Oncol. Biol. Phys., vol. 72, No. 4, 2008, pp. 996-1001.

Duthoy, W., et al., "Clinical implementation of intensity-modulated arc therapy (IMAT) for rectal cancer," Int. J. Radiat. Oncol. Biol. Phys., vol. 60, No. 3, 2004, pp. 794-806.

(56) References Cited

OTHER PUBLICATIONS

Lagerwaard F.J., et al., Whole-brain radiotherapy with simultaneous integrated boost to multiple brain metastases using volumetric modulated arc therapy, Int. J. Radiat. Oncol. Biol. Phys., vol. 75, No. 1, 2009, pp. 253-259.

Popescu, C.C., et al., "Volumetric modulated arc therapy improves dosimetry and reduces treatment time compared to conventional intensity-modulated radiotherapy for locoregional radiotherapy of left-sided breast cancer and internal mammary nodes," Int. J. Radiat. Oncol. Biol. Phys., vol. 76, No. 1, 2009, pp. 287-295.

Clarke M., et al., "Effects of radiotherapy and of differences in the extent of surgery for early breast cancer on local recurrence and 15-year survival: An overview of the randomised trials," Lancet, vol. 366, 2005, pp. 2087-2106.

Paszat, L.F., et al., "Mortality from myocardial infarction following post lumpectomy radiotherapy for breast cancer. A population-based study in Ontario, Canada," Int. J. Radiat. Oncol. Biol. Phys., vol. 43, No. 4, 1999, pp. 755-762.

Baglan, Kathy L. et al., "Accelerated partial breast irradiation using 3D conformal radiation therapy (3D-CRT)," Int J Radiat Oncol Biol Phys, vol. 55, No. 2, 2003, pp. 302-311.

Pignol, J., et al., "A multicenter randomized trial of breast intensity-modulated radiation therapy to reduce acute radiation dermatitis," J. Clin. Oncol., vol. 26, No. 13, 2008, pp. 2085-2092.

Reeder, R., et al., "Predictors for clinical outcomes after accelerated partial breast intensity-modulated radiotherapy", Int. J. Radiat. Oncol. Biol. Phys., vol. 74, No. 1, 2009, pp. 92-97.

Hall, E.J., et al., "Radiation-induced second cancers: The impact of 3D-CRT and IMRT," Int J Radiat. Oncol. Biol. Phys., vol. 56, No. 1, 2003, pp. 83-88.

Shaitelman, S.F., et al., "Continuous Arc Rotation of the Couch Therapy for the Delivery of Accelerated Partial Breast Irradiation: A Treatment Planning Analysis," Int. J. Radiat. Oncol. Biol. Phys., vol. 80, No. 3, 2011, pp. 771-778.

Takahashi, S., "Conformation Radiotherapy. Rotation Techniques as Applied to Radiography and Radiotherapy of Cancer," Acta Radiol, Diagn (Stockh), Suppl 242:1+, 1965, pp. 11-140.

Kim, L., et al., "Volumetric Modulated Arc Therapy Using a Rotating Couch: An Accelerated Partial Breast Irradiation Planning Study," Int. L. Radiation Oncology Biol. Phys., vol. 75, Issue 3, Supplement 1, Nov. 1, 2009, pp. S732-S733.

Burgess, L., et al., "Partial Brain VMAT Planning Using Simultaneous Couch and Gantry Arcs," Int. L Radiat. Oncol. Biol. Phys., vol. 78, Issue 3, Supplement 1, 2010, pp. S818-S819.

International Search Report and Written Opinion for International Application No. PCT/US2011/000006, mailed Mar. 1, 2011.

Wong, J.W., et al., "Reconsideration of the Power-Law (Batho) Equation for Inhomogeneity Corrections", Med. Phys., Jul./Aug. 1982, vol. 9, No. 4, pp. 521-530.

Wong, J.W., et al., "Second Scatter Contribution to Dose in Cobalt-60 Beam" Med. Phys., Nov./Dec. 1981, vol. 8, No. 6, pp. 775-782.

Wong, J.W., et al., "The Cumulative Verification Image Analysis Tool for Offline Evaluation of Portal Images", Int. J. Radial. Oncol.Biol. Phys., 1995, vol. 33, No. 5, pp. 1301-1310.

Wong, J.W., et al., "The Use of Active Breathing Control (ABC) to Reduce Margin for Breathing Motion", Int. J. Radiol. Oncol. Biol. Phys., 1999, vol. 44, No. 4, pp. 911-919.

Wong, J.W., et al., "Treatment Verifications and Patient Dose Estimations Using Portal Dose Imaging" Radiotherapy System Research (Japan). 1988; vol. 5, No. 3, pp. 213-225.

Wong, J.W., et al.; "A New Approach to CT Pixel-Based Photon Dose Calculations in Heterogeneous Media", Med. Phys., Mar./Apr. 1983, vol. 10, No. 2, pp. 199-208.

Wu, Y., et al., "Implementing multiple static field delivery for intensity modulated beams", Med. Phys., Nov. 2001, vol. 28, No. 11, pp. 2188-2197.

Xu, Xiaochao, et al., "A Tetrahedron Beam Computed Tomography Benchtop System With a Multiple Pixel Field Emission X-Ray Tube," Med. Phys., vol. 3, No. 10, 2001, pp. 5500-5508.

Yan, D., "Adapt Radiotherapy to Temporal Biological Targets Assessed Using Biological Images," publication source unknown, while the date of publication is unknown, it is believe that the article was publicly available before May 24, 2007, 3 pages.

Yan, D., "Image-Guided Adaptive Radiotherapy Model," AAPM, Mar. 10, 2006, pp. 1-15.

Yan, D., "Image-Guided/Adaptive Radiotherapy," Medical Radiology-Radiation Oncology, Volume: New Technologies in Radiation Oncology, Edited by W. Schlegel, T. Bortfeld and Al Grosu, Springer-Verlag, Berlin, Heidelberg, New York, Hong Kong, Sep. 8, 2005, ISBN 3-540-00321-5, pp. 317-332.

Yan, D., "Treatment Strategy for Daily Image Feedback Adaptive Radiotherapy," Proceeding, XIIIth International Conference on the Use of Computers in Radiotherapy, Heidelberg, Germany, 2000, pp. 518-520.

Yan, D., et al., "A Model to Accumulate Fractionated Dose in a Deforming Organ," Int. J. Radiation Oncology Biol. Phys., vol. 44, No. 3, 1999, pp. 665-675.

Yan, D., et al., "A New Model for "Accept or Reject" Strategies in Off-Line and On-Line Megavoltage Treatment Evaluation", Int. J. Radiat. Oncol. Biol. Phys., 1995, vol. 31, No. 4, pp. 943-952.

Yan, D., et al., "Adaptive Modification of Treatment Planning to Minimize the Deleterious Effects of Treatment Setup Errors," Int. J. Radiation Oncology Biol. Phys., vol. 37, No. 5, white the publication date is unknown, it is believed to have been published prior to 1999, pp. 1-27.

Yan, D., et al., "Adaptive Modification of Treatment Planning to Minimize the Deleterious effects of Treatment Setup Errors", Int. J. Radiat. Oncol. Biol. Phys., 1997, vol. 38, No. 1, pp. 197-206.

Yan, D., et al., "Adaptive Radiation Therapy," Phys. Med. Biol., vol. 42, 1997, pp. 123-132.

Yan, D., et al., "An Off-Line Strategy for Constructing a Patient-Specific Planning Target Volume For Image Guided Adaptive Radiotherapy of Prostate Cancer," Int. J. Radiation Oncology Biol. Phys., vol. 48, No. 1, 2000, pp. 289-302.

Yan, D., et al., "Computed Tomography Guided Management of Interfractional Patient Variation," Semin. Radial Oncol. vol. 15, 2005, pp. 168-179.

Yan, D., et al., "Organ/Patient Geometric Variation in External Beam Radiotherapy and its Effect," Med. Phys., vol. 28, No. 4, Apr. 2001, pp. 593-602.

Yan, D., et al., "Strategies for Off-Line and On-Line Image Feedback Adaptive Radiotherapy," Editors: BK Paliwal, DE Herbert, JF Fowler, MP Mehta, Biological & Physical Basis of IMRT & Tomotherapy, AAPM Symposium Proceeding No. 12, 2002, pp. 139-150.

Yan, O., et al., "The influence of interpatient and intrapatient rectum variation on external beam treatment of prostate cancer", Int. J. Radiat. Oncol. Biol. Phys. 2001, vol. 51, No. 4, pp. 1111-1119.

Yan, D., et al., "The Use of Adaptive Radiation Therapy to Reduce Setup Error: A Prospective Clinical Study," Int. J. Radiation Oncology Biol. Phys., vol. 41, No. 3, 1998, pp. 715-720.

Yang, Y., et al., "Evaluation of On-Board kV Cone Beam CT (CBCT)-based Dose Calculation," Phys. Med. Biol., vol. 52, 2007, pp. 685-705.

Ying, X.G., et al., "Portal Dose Images. II: Patient Dose Estimation", Int. J. Radiat. Oncol. Biol. Phys., Jun. 1990, vol. 18, No. 6, pp. 1465-1475.

Yu, C.X., et al., "A Method for Implementing Dynamic Photon Beam Intensity Modulation Using Independent Jaws and a Multileaf Collimator", Phys. Med. Biol., 1995, vol. 40, pp. 769-787.

Yu, C.X., et al., "A Multiray Model for Calculating Electron Pencil Beam Distribution", Med. Phys., Sep./Oct. 1988, vol. 15, No. 5, pp. 662-671.

Yu, C.X., et al., "Photon Dose Calculation Incorporating Explicit Electron Transport", Med. Phys., Jul. 1995, vol. 22, No. 7, pp. 1157-1165.

Yu, C.X., et al., "Photon Dose Perturbations Due to Small Inhomogeneities", Med. Phys., Jan./Feb. 1987, vol. 14, No. 1, pp. 78-83.

Zeng, G.L., et al., "Image Reconstruction Algorithm for a SPECT System with a Convergent Rotating Slat Collimator," IEEE Transactions on Nuclear Science, vol. 51, No. 1, 2004, pp. 142-148.

(56) References Cited

OTHER PUBLICATIONS

Zhang, J., et al., "A Multi-Beam X-Ray Imaging System Based on Carbon Nanotube Field Emitters," Medical Imaging 2006: Physics of Medical Imaging Proceedings of SPIE, vol. 6142, 2006, eight pages.

Zhang, T., et al., "Automatic Delineation of Online Head and Neck CT Images: Towards Online Adaptive Radiotherapy," Int. J. of Radiation Oncology Biol. Phys., vol. 68, No. 2, 2007, pp. 522-530.

Zhang, Tiezhi, et al., "Tetrahedron Beam Computed Tomography (TBCT): A New Design of Volumetric CT System," Phys. Med. Biol., vol. 54, 2009, pp. 3365-3378.

International Search Report for PCT/US2007/008996, dated Mar. 4, 2008, three pages.

International Search Report for PCT/US2007/012607, dated Apr. 11, 2008, two pages.

Vicini, F., et al., "NSABP B-39/RTOG 0413: A randomized phase III study of conventional whole breast irradiation versus partial breast irradiation for women with Stage 0, I, or II breast cancer," [version Mar. 13, 2007] Available from: http://rtog.org/members/protocols/0413/0413.pdf, publicly available as of Nov. 23, 2009, pp. 1-122.

Hepel, J. T., et al., "Toxicity of three-dimensional conformal radiotherapy for accelerated partial breast irradiation," Int. J. Radiat. Oncol. Biol. Phys., vol. 75, No. 5, 2009, pp. 1290-1296.

Jagsi, Reshma et al. "Unacceptable cosmesis in a protocol investigating intensity modulated radiotherapy with active breathing control for accelerated partial breast irradiation" Int. J. Radiat. Oncol. Biol. Phys. vol. 76, No. 1, 2009, pp. 71-78.

Livi, L., et al., "Accelerated partial breast Irradiation with IMRT: new technical approach and interim analysis of acute toxicity in a phase III randomized clinical trial," Int. J. Radiat. Oncol. Biol. Phys., vol. 77, No. 2, 2010, pp. 509-515.

Smith, Benjamin D., et al., "Accelerated partial breast irradiation consensus statement from the american society for radiation oncology (ASTRO)," Int. J. Radiat. Oncol. Biol. Phys., vol. 74, No. 4, 2009, pp. 987-1001.

Veronesi, Umberto, et al., "Twenty year follow-up of a randomized study comparing breast-conserving surgery with radical mastectomy for early breast cancer," N. Engl. J. Med., vol. 347, No. 16, Oct. 17, 2002, pp. 1227-1232.

Jain, A.K., et al., "Does three-dimensional external beam partial breast irradiation spare lung tissue compared with standard whole breast irradiation?" Int. J. Radiat. Oncol. Biol. Phys., vol. 75, No. 1, 2009, pp. 82-88.

Recht, A., et al., "Lung dose-volume parameters and the risk of pneumonitis for patients treated with accelerated partial-breast irradiation using three-dimensional conformal radiotherapy," J. Clin. Oncol., vol. 27, No. 24, 2009, pp. 3887-3893.

Low, J.A., et al., "Long-term follow-up for locally advanced and Inflammatory breast cancer patients treated with multimodality therapy," J. Clin. Oncol., vol. 22, No. 20, 2004, pp. 4067-4074.

Romond, Edward H., et al., "Trastuzumab plus adjuvant chemotherapy for operable HER2—positive breast cancer," N. Engl. J. Med., vol. 353, No. 16, Oct. 20, 2005, pp. 1673-1684.

Piccart-Gebhart, M.J., et al., "Trastuzumab after adjuvant chemotherapy in HER2—positive breast cancer," N. Engl. J. Med., vol. 353, No. 16, 2005, pp. 1659-1672.

Berrington de Gonzalez, A., et al., "Second solid cancers after radiotherapy for breast cancer in SEER cancer registries," Br. J. Cancer 2009, vol. 102, No. 1, Jan. 5, 2010, pp. 220-226.

Stovall, M., et al., "Dose to the contralateral breast from radiotherapy and risk of second primary breast cancer in the WECARE study," Int. J. Radiat. Oncol. Biol. Phys., vol. 72, No. 4, 2008, pp. 1021-1030.

Kozak, K.R., et al., "Dosimetric comparison of two different three-dimensional conformal external beam accelerated partial breast irradiation techniques," Int. J. Radiat. Oncol. Biol. Phys., vol. 65, No. 2, 2006, pp. 340-346.

Rusthoven, K.E., et al., "Accelerated partial-breast intensity-modulated radiotherapy results in improved dose distribution when compared with three-dimensional treatment-planning techniques," in J. Radiat. Oncol. Biol. Phys., vol. 70, No. 1, 2008, pp. 296-302.

Lockman, D., et al., "Estimating the Dose Variation in a Volume of Interest with Explicit Consideration of Patient Geometric Variation," Med. Phys., vol. 27, No. 9, Sep. 2000, pp. 2100-2108.

Lucas, "Analysis of surface dose variation in CT procedures." The British Journal of Radiology, 74 (2001), 1128-1136.

Martinez, A., et al., "Improvement in dose escalation using the process of adaptive radiation therapy combined with three dimensional conformal or Intensity modulated beams for prostate cancer", Int. J. Radiat. Oncol. Biol. Phys. 2001, vol. 50, No. 5, pp. 1226-1234.

Masterson, M.E., et al., "Inter-Institutional Experience in Verification of External Photon Dose Calculations", Int. J. Rad. Oncol. Biol. Physics, 1991, vol. 21, pp. 37-58.

Michalski, J., et al., "An Evaluation of Two Methods of Anatomical Alignment of Radiotherapy Portal Images", Int. J. Radiat. Oncol. Biol. Phys., 1993; vol. 27. No. 5, pp. 1199-1206.

Michalski, J.M., et al., "Prospective Clinical Evaluation of an Electronic Portal Imaging Device", Int. J. Radiat. Oncol. Biol. Phys., 1996, vol. 34, No. 4, pp. 943-951.

Michalski, J.M., et al., "The Use of On-Line Image Verification to Estimate the Variation in Radiation Therapy Dose Delivery", Int. J. Radiat. Oncol. Biol. Phys., 1993, vol. 27, No. 3, pp. 707-716.

Milliken, B.D., et al., "Verification of the Omni Wedge Technique", Med. Phys. Aug. 1998, vol. 25, No. 8, pp. 1419-1423.

Mohan, R. (writing chair), "Three-Dimensional Dose Calculations for Radiation Treatment Planning", Int. J. Rad. Oncol. Biol. Physics, May 15, 1991; vol. 21, No. 1, pp. 25-36.

Mueller, K., et al., "Cone-Beam Computed Tomography (CT) for a Megavoltage Linear Accelerator (LINAC) Using an Electronic Portal Imaging Device (EPID) and the Algebraic Reconstruction Technique (ART)," publication source unknown, (publication date unknown), 4 pages, while the date of publication is unknown, it is believe that the article was publicly available before May 24, 2007.

Nakagawa, K. et al., "Development of a megavoltage ct scanner using linear accelerator treatment beam", Journal of JASTRO, vol. 3, No. 4, pp. 265-276, 1991, Japanese Society for Therapeutic Radiology and Oncology.

Oldham, M., et al., "Practical aspects of in situ 160(y,n)150 activation using a conventional medical accelerator for the purpose of perfusion imaging", Med. Phys. Aug. 2001; vol. 28, No. 8, pp. 1669-1678.

Perera, H., et al., "Rapid Two-Dimensional Dose measurement in Brachytherapy Using Plastic Scintillator Sheet: Linearity, Signal-to-Noise Ratio, and Energy Response Characteristics.", Int. J. Radiat. Onco1. Biol. Phys., 1992, vol. 23, No. 5, pp. 1059-1069.

Pisani, L., et al., "Setup Error in Radiotherapy: On-line Correction Using Electronic Kilovoltage and Megavoltage Radiographs", Int. J. Radiat. Oncol. Biol. Phys., 2000, vol. 47, No. 3, pp. 825-839.

Purdy, J.A., et al., "State of the Art High Energy Photon Treatment Planning", Front Radiat. Ther. Oncol., 1987, vol. 21, pp. 4-24.

Schaly, B., et al., "Tracking the Dose Distribution in Radiation Therapy by Accounting for Variable Anatomy," Phys. Med. Biol., vol. 49, 2004, pp. 791-805.

Schmidt, T.G., et al., "A Prototype Table-Top Inverse-Geometry Volumetric CT Images," Med. Phys., vol. 33, No. 6, 2006, pp. 1867-1878.

Sharpe, M.B., et al., "Compensation of X-Ray Beam Penumbra in Conformal Radiotherapy", Med. Phys., Aug. 2000, vol. 27, No. 8, pp. 1739-1745.

Sharpe, M.B., et al., "Monitor Unit Settings for Intensity Modulated Beams Delivered Using a Step-and-Shoot Approach", Med. Phys., Dec. 2000, vol. 27, No. 12, pp. 2719-2725.

Shikhaliev, P.M., et al., "Photon Counting Computed Tomography: Concept and Initial Results," Med. Phys., vol. 32, No. 2, 2005, abstract.

Shirato, H., "Real-time tumor tracking radiotherapy and stereotactic irradiation", Monthly New Medical Care, vol. 26, No. 12, pp. 61-63, 1999, ME Co., Ltd.

Shiu, A.S., et al., "Verification Data for Electron Beam Dose Algorithms", Med. Phys., May/Jun. 1992, vol. 19, No. 3, pp. 623-636.

Siewerdsen, et al., "Cone-Beam Computed Tomography with a Flat-Panel Imager. Effects of Image Lag," Med. Phys., vol. 26, No. 12, Dec. 1999, pp. 2635-2647.

(56) References Cited

OTHER PUBLICATIONS

Siewerdsen, et al., "Cone-Beam CT with a Flat-Panel Imager. Noise Consideration for Fully 3-D Computed Tomography," SPIE Physics of Medical Imaging, vol. 3336, Feb. 2000, pp. 546-554.

Siewerdsen, et al., "Optimization of X-Ray Imaging Geometry (with Specific Application to Flat-Panel Cone-Beam Computed Tomography)," Non-Final Version of Manuscript to be published in Med. Phys., vol. 27, No. 8, Aug. 2000, pp. 1-12.

Siewerdsen, J.H., et al., "A Ghost Story: Spatio—Temporal Response Characteristics of an Indirect-Detection Flat-Panel Imager", Med. Phys., Aug. 1999, vol. 26, No. 8, pp. 1624-1641.

Siewerdsen, J.H., et al., "Cone-Beam Computed Tomography with a Flat-Panel Imager: Magnitude and Effects of X-Ray Scatter", Med. Phys., Feb. 2001, vol. 28, No. 2, pp. 220-231.

Siewerdsen, J.H., et al., "Empirical and Theoretical Investigation of the Noise Performance of Indirect Detection, Active Matrix Flat-Panel Imagers (AMFPIs) for Diagnostic Radiology", Med. Phys., Jan. 1997, vol. 24, No. 1, pp. 71-89.

Siewerdsen, J.H., et al., "Optimization of X-Ray Imaging Geometry (with Specific Application to Flat-Panel Cone-Beam Computed Tomography)", Med. Phys., Aug. 2000, vol. 27, No. 8, pp. 1903-1914.

Siewerdsen, JH, et al., "Signal, Noise Power Spectrum, and Detective Quantum Efficiency of Indirect-Detection Flat-Panel Panel Imagers for Diagnostic Radiology", Med. Phys., May 1998, vol. 25, No. 5, pp. 614-628.

Sohn, M. et al., "Modeling Individual Geometric Variation Based on Dominant Eigenmodes of Organ Deformation: Implementation and Evaluation," Phys Med Biol, vol. 50, 2005, pp. 5893-5908.

Sontag, M.R. and Purdy, J.A. (writing chairs), "State of the Art of External Photon Beam Radiation Treatment Planning", Int. J. Rad. Oncol. Biol. Physics. 1991, vol. 21 No. 1, pp. 9-23.

Stromberg, J.S., et al., "Active Breathing Control (ABC) for Hodgkin's Disease: Reduction in Normal Tissue Irradiation with Deep Inspiration and Implications for Treatment", Int. J. Radiat. Oncol. Biol. Phys. 2000, vol. 48, No. 3, pp. 797-806.

Teicher, B.A., et al., "Allosteric Effectors of Hemoglobin as Modulators of Chemotherapy and Radiation Therapy In Vitro and In Vivo", Cancer Chemother. Pharmacol., 1998, vol. 42, pp. 24-30.

Tepper, J.E. and Shank, B. (Writing Chairs), "Three-Dimensional Display in Planning Radiation Therapy: A Clinical Perspective", Int. J. Rad. Oncol. Biol. Physics. 1991, vol. 21, No. 1, pp. 79-89.

Urie, M.M., et al., "The Role of Uncertainty Analysis in Treatment Planning", Int. J. Radiat. Oncol. Biol. Phys., 1991, vol. 21, No. 1, pp. 91-107.

Vicini, F.A., et al., "Dose-Volume Analysis for Quality Assurance of Interstitial Brachytherapy for Breast Cancer", Int. J. Radiat. Oncol. Biol. Phys., 1999, vol. 45, No. 3, pp. 803-810.

Vicini, F.A., et al., "Implementation of a 3D-Virtual Brachytherapy in the Management of Breast Cancer: a Description of a New Method of Interstitital Brachytherapy", Int. J. Radial. Oncol. Biol. Phys., 1998, vol. 40, No. 3, pp. 629-635.

Vicini, F.A., et al., "Low-Dose-Rate Brachytherapy as the Sole Radiation Modality in the Management of Patients with Early-Stage Breast Cancer Treated with Breast-Conceiving Therapy: Preliminary Results of a Pilot Trial", Int. J. Radial. Oncol. Biol. Phys., 1997, vol. 38, No. 2, pp. 301-310.

Webb, S., et al., Abstract of "Monte Carlo Modelling of the Performance of a Rotating Slit-collimator for Improved Planar Gamma-Camera Imaging," Phys. Med. Biol., vol. 37, No. 5, 1992, abstract.

Weinberg, R., et al., "Dosimetric Uncertainties of Three-Dimensional Dose Reconstruction from Two-Dimensional Data in a Multi-Institutional Study," Journal of Applied Clinical Medical Physics, vol. 5, No. 4, Fall 2004, pp. 15-28.

Williamson, J.F., et al., "One-Dimensional Scatter-Subtraction Method for Brachytherapy Calculation Near Bounded Heterogeneities", Med. Phys., Jan./Feb. 1993, vol. 20, No. 1, pp. 233-244.

Wong, J.K., et al., "Conservative Management of Osteoradionecrosis", Oral Surg. Oral Med. Pahol. Oral Pathol., Jul. 1997, vol. 84, No. 1, pp. 16-21.

Wong, J.W., (Writing chair), "Role of Inhomogeneity Corrections in 3D Photon Treatment Planning", Int. J. Rad. Oncol. Biol. Physics. 1991, vol. 21, No. 1, pp. 59-69.

Wong, J.W., et al., "Development of a Second-Generation Fiber-Optic On-Line Image Verification System", Int. J. Radiat. Oncol. Biol. Phys., 1993, vol. 26, No. 2, pp. 311-320.

Wong, J.W., et al., "Effect of Small Inhomogeneities on Dose in a Cobalt-60 Beam", Med. Phys., Nov./Dec. 1981, vol. 8, No. 6, pp. 783-791.

Wong, J.W., et al., "On Methods of Inhomogeneity Corrections for Photon Transport", Med. Phys., Sep./Oct. 1990, vol. 17, No. 5, pp. 807-814.

Wong, J.W., et al., "On-Line Image Verification in Radiation Therapy: An Early USA Experience", Med. Prog. Through Technol., 1993, vol. 19, pp. 43-54.

Wong, J.W., et al., "On-Line Radiotherapy Imaging with an Array of Fiber-Optic Image Reducers", Int. J. Radiat. Oncol. Biol. Phys., Jun. 1990, vol. 18, No. 6, pp. 1477-1484.

Wong, J.W., et al., "Portal Dose Images. I: Quantitative Treatment Plan Verification", Int. J. Radiat. Oncol.Biol.Phys., Jun. 1990, vol. 18, No. 6, pp. 1455-1463.

Japanese Office Action Notification of Grounds for Refusal for JP Application No. 2001-559337, Jan. 15, 2015, 5 pages.

Yasuda, T., State of the Art and Future Possibility of Image Application in Medicine, ITEJ Technical Report, Jul. 23, 1992, pp. 1-8, vol. 16 No. 47.

Inamura, S., Future for Digital X-Ray, Monthly New Medical Care, Apr. 1, 1999, pp. 72-78, vol. 26 No. 4.

\* cited by examiner

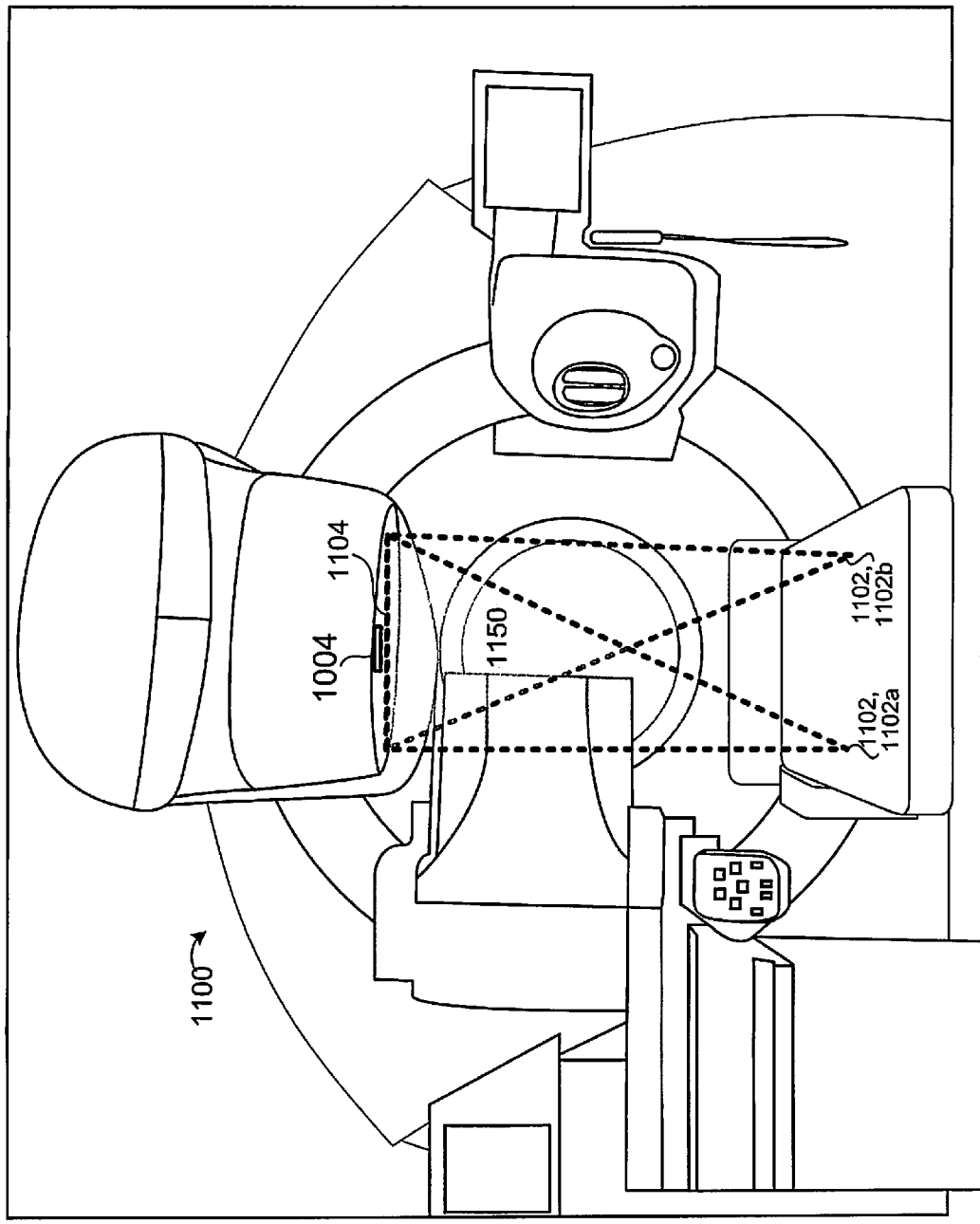

IMAGE GUIDED RADIOTHERAPY WITH DUAL SOURCE AND DUAL DETECTOR ARRAYS TETRAHEDRON BEAM COMPUTED TOMOGRAPHY

CROSS REFERENCE TO RELATED APPLICATIONS

The present application claims priority under 35 U.S.C. §119(e) to U.S. Provisional Application 61/822,036, filed on May 10, 2013. This application is also a continuation-in part application of U.S. patent application Ser. No. 13/194,215, filed on Jul. 29, 2011, currently pending, which is a continuation-in-part application of U.S. patent application Ser. No. 12/803,480, filed on Jun. 29, 2010, currently pending, which is a continuation application of U.S. patent application Ser. No. 11/786,781, filed on Apr. 12, 2007, now U.S. Pat. No. 7,760,849, which claims, under 35 U.S.C. §119(e), the benefit of priority of the filing date of Apr. 14, 2006, of U.S. Provisional Patent Application Ser. No. 60/792,207, filed on the aforementioned date, the entire contents of each of the above mentioned patent and patent applications are incorporated herein by reference. The disclosures of these prior applications are considered part of the disclosure of this application and are hereby incorporated by reference in their entireties.

TECHNICAL FIELD

This disclosure relates to a radiation treatment machine combined with computed tomography (CT) and, more particularly, to a volumetric computed tomography (VCT) system, or more explicitly, to a tetrahedron beam computed tomography (TBCT) system.

BACKGROUND

Radiation therapy, also known as radiotherapy, is the medical use of ionization radiation as part of cancer treatment. Such treatment includes controlling or killing malignant cells. The amount of radiation used in radiation therapy is measured in Gray (Gy) and varies based on the type and stage of cancer being treated. Therefore, doctors plan the type and amount of radiation given to a patient based on the type of cancer in addition to considering the patient's health, age, weight and other factors.

Currently, in radiotherapy clinics, advanced treatment planning and delivery methods include increasing the radiation dose to reach the maximum tolerance that a normal tissue endures. To achieve such advanced treatment, there is an increase in demand for radiation methods that provide highly precise localization and motion control both before and during radiation treatment. Image-guided radiation therapy (IGRT) is critically important for the delivery of highly conformal radiation doses. In addition, advanced treatment techniques such as online and offline adaptive radiotherapy cannot be implemented without the motion information provided by online imaging modalities.

Computed tomography (CT) has become an important volumetric imaging modality for IGRT. CT imaging provides a transverse image of an object. Conventional fan beam CT uses a point x-ray source and a linear detector array. The detector array may have one or more detector rows. With a single rotation, one or more image slices can be reconstructed using computer algorithms. Different CT techniques may be used for the different treatment modalities. In some examples, a megavoltage fan beam CT (MVCT) is used for a helical tomotherapy system. In other examples, a megavoltage cone beam CT (MV-CBCT) is used. The major drawbacks of MVCT are lack of soft tissue contrast and high imaging dose due to the high x-ray energy. One improvement made to the MV-CBCT system is the use of a low atomic number target, such as carbon to shift the bremsstrahlung spectrum to the lower energy range. Another improvement is the development of CT on-rail systems, in which a diagnostic helical CT scanner is installed in the treatment room for IGRT purposes. During the IGRT treatment, the bed where the patient lies is rotated by an angle, usually 180 degrees, to align with the path of the rails on which the CT scanner is mounted and then rotated back to the treatment position after imaging is complete. While this system provides superior image quality, it is not a popular imaging modality mainly because it is inconvenient for the patient and lacks intra-treatment imaging capability (the organ movement within one treatment on a given day).

Kilovoltage (kV) cone-beam CT (CBCT) is an online volumetric imaging modality used for LINAC-based radiation treatments. The kV CBCT system includes a radiographic kV x-ray tube and a flat panel imager (FPI). The kV apparatus is installed on an additional structure that is orthogonal to the MV treatment beam. The kV CBCT system is convenient to use, allows the patient to remain in the same position for both imaging and treatment, and provides better soft tissue contrast than the megavoltage modalities. However, despite these advantages, specifically the convenience to the patient, the performance of the kV CBCT system is still not ideal. Excessive scatter photons are a major problem for CBCT, and the performance of the FPI is inferior to that of helical CT scanners. Another, but less significant problem is that CBCT suffers from approximate reconstruction artifacts at large cone angles because the circular trajectory of the system does not meet the data sufficiency condition. Because of its inferior image quality, clinical uses of CBCT are mostly restricted to localization in IGRT treatments. The inferior image quality also limits its use for advanced IGRT treatment techniques, such as online and offline adaptive radiotherapy, in which soft tissue contrast is important for deformable image registration and segmentation. Furthermore, the reconstruction artifacts and excessive scatter in CBCT make it difficult to accurately calibrate CT numbers, which poses a challenge to the use of CBCT images for dose calculation.

In addition to volumetric imaging, real-time imaging is also desirable in order to monitor intra-fraction motion, which is the organ movement during radiation delivery. While the fluoroscopic imaging function of CBCT may be used for real-time tracking, a single kV beam positioned orthogonally to the megavoltage (MV) beam is not an optimal configuration. This configuration is insensitive to motion that is orthogonal to the MV beam and may result in geometric miss during treatment delivery. MV portal imaging may be used, but in many situations, the image quality produced by the MV beam is insufficient to detect relevant anatomical features or fiducial markers. Alternatively, the gantry may be rotated by 90 degrees to acquire images at two different angles and create a stereoscopic view. However, since the two images would not be taken simultaneously, this method does not provide real-time stereoscopic imaging and therefore cannot be used for monitoring respiratory motion. Other developers have developed a real-time stereoscopic imaging modality for IGRT by mounting two kV x-ray source and FPI detector pairs on the floor and ceiling of the treatment room. Unfortunately, this method does not have the capability to perform volumetric CT imaging.

The current CBCT systems with one point source and one flat panel imager are not able to provide stereoscopic imaging functionality. Their fluoroscopic imaging function cannot detect motion along the kV beam direction. When the kV beam is orthogonal to the MV beam, this motion component can cause geometric miss of the target as shown in FIGS. 1A and 1B.

SUMMARY

One aspect of the disclosure provides a radiation treatment and imaging system for emitting a radiation beam and X-ray beams towards an object or target (e.g., an organ or a tumor in a patient). The radiation treatment and imaging system includes a first x-ray source, a first detector, a first collimator, first and second detectors, a linear accelerator, a data processing device, and a display. The first x-ray source array emits a first plurality of x-ray beams (e.g, from at least one source) at different positions along a scanning direction. The first collimator intercepts the first plurality of x-ray beams emitted by the first x-ray source so that a first plurality of fan-shaped x-ray beams emanate from the first collimator towards the object. The first detector receives a first portion of the first plurality of x-ray beams emitted by the first x-ray source and generates a first imaging signal based on the first portion of the first plurality of x-ray beams. The second detector receives a second portion of the first plurality of x-ray beams emitted by the first x-ray source and generates a second imaging signal based on the second portion of the first plurality of x-ray beams. The linear accelerator delivers a radiation beam from a megavolt radiation source to the object. The megavolt radiation source is positioned between the first and second detectors and emits treatment radiation beams in a direction in-line with the first x-ray beams. The data processing device is in communication with the first and second detectors. The data processing device receives the first and second imaging signals, where the first x-ray source array, the first and second detectors, and the linear accelerator rotate about a rotation axis causing the data processing device to receive more than one first and second imaging signals. Moreover, the data processing device reconstructs the received imaging signals generating a three-dimensional tetrahedron beam computed tomography image therefrom. Finally, the display is in communication with the data processing device and displays the three-dimensional tetrahedron beam computed tomography (TBCT) image.

Implementations of the disclosure may include one or more of the following features. In some implementations, the first x-ray source array is orthogonal to the first and second detectors. In other implementations, the first x-ray source array sequentially emits the first plurality of x-ray beams.

In some implementations, the system further includes a second x-ray source array emitting a second plurality of x-ray beams at different positions along a scanning direction, and a second collimator intercepting the second plurality of x-ray beams emitted by the second x-ray source so that a second plurality of fan-shaped x-ray beams emanate from the first collimator towards the object. The first detector receives a first portion of the second plurality of x-ray beams emitted by the second x-ray source. The generated first imaging signal is based on the first portion of the first plurality of x-ray beams and the first portion of the second plurality of x-ray beams. The second detector receives a second portion of the second plurality of x-ray beams emitted by the second x-ray source. The generated second imaging signal is based on the second portion of the first plurality of x-ray beams and the second portion of the second plurality of x-ray beams. In some examples, the first and second x-ray source arrays are orthogonal to the first and second detectors. In other examples, the second x-ray source array sequentially emits the second plurality of x-ray beams.

In some implementations, the linear accelerator includes an electronic portal imaging device in communication with the data processing device, the first and second x-ray source arrays positioned on either side of the electronic portal imaging device.

Another aspect of the disclosure provides a radiation treatment and imaging system for emitting a MV x-ray radiation treatment beam and kV x-ray imaging beams towards an object. The radiation treatment and imaging system includes a linear accelerator and a tetrahedron beam computed tomography (TBCT) system. The linear accelerator delivers a MV radiation beam from a radiation source to the object, while the TBCT system is used for imaging the object before and/or during radiation treatments. The tetrahedron beam computed system includes first and second x-ray source arrays, first and second collimators, and first and second detector arrays. The first x-ray source array emits a first and third plurality of kV x-ray beams at different positions along a first scanning direction, and the first collimator intercepts the first and third plurality of x-ray beams so that fan-shaped kV x-ray beams emanate from the first collimator towards the object. The second x-ray source array emits second and fourth pluralities of kV x-ray beams at different positions along a second scanning direction, and a second collimator that intercepts the second and fourth pluralities of kV x-ray beams so that fan-shaped x-ray beams emanate from the second collimator towards the object. The first detector receives: 1) the first plurality of fan-shaped kV x-ray beams from the first x-ray source array; and 2) the second plurality of fan-shaped kV x-ray beams from the second x-ray source array after they pass through the object. Moreover, the first detector generates first and second imaging signals for each of the received first and second pluralities of fan-shaped kV x-ray beams from the first and second kV x-ray source arrays, respectively. The second detector receives a third plurality of fan-shaped x-ray beams from the first x-ray source array and a fourth plurality of fan-shaped x-ray beams from the second x-ray source array after they pass through the object. In addition, the second detector generates third and fourth imaging signals for each of the received third and fourth pluralities of fan-shaped kV x-ray beams from the first and second x-ray source arrays, respectively.

A computing processor (e.g., computer) is connected to the first and the second detectors and receives the first imaging signals for each of the first plurality of fan-shaped x-ray beams received by the first detector, the second imaging signals for each of the second plurality of fan-shaped x-ray beams received by the first detector, the third imaging signals for each of the third plurality of fan-shaped x-ray beams received by the second detector, and the fourth imaging signals for each of the fourth plurality of fan-shaped x-ray beams received by the second detector. The first x-ray source array, the second x-ray source array, the first detector and second detectors rotate about a rotation axis so as to rotate about the object so that multiple imaging signals are reconstructed by the computer to generate a three-dimensional tetrahedron beam computed tomography image therefrom. Furthermore, a display is connected to the computer and displays the three-dimensional computed tomography image and two-dimensional radiographic images. The MV radiation treatment source is positioned between the first and second detectors and emits MV radiation treatment beams in a direction in-line with the central axis of kV x-ray imaging beams.

In some implementations, the linear accelerator includes an electronic portal imaging device in communication with the computer where the first and second x-ray source arrays are positioned on either side of the electronic portal imaging device or where the first and second detector arrays are positioned on either side of the electronic portal imaging device. The first and second x-ray source arrays are orthogonal to the first and second detectors. In some examples, each of the source and detector array pairs generates a projection image. Up to four projection images can be generated by the two source arrays and two detector arrays. In some examples, each of the projection image views the object in different angles. Projection images at different angles form stereoscopic views. In some examples, the kV x-ray beams share the same central axis as the MV treatment beam.

Another aspect of the disclosure provides a method of forming a stereoscopic image. The method includes positioning a therapy radiation source between a first detector and a second detector. The method includes: emitting a first plurality of kilovolt x-ray beams from a first x-ray source array; intercepting the first plurality of kilovolt x-ray beams so that fan-shaped x-ray beams emanate towards the object; emitting a second plurality of kilovolt x-ray beams from a second x-ray source array at different positions; and intercepting the second plurality of kilovolt x-ray beams so that fan-shaped x-ray beams emanate towards the object. The method also includes: emitting a third plurality of kilovolt x-ray beams from the first x-ray source array; intercepting the third plurality of kilovolt x-ray beams so that fan-shaped kilovolt x-ray beams emanate towards the object; emitting a fourth plurality of kilovolt x-ray beams from the second x-ray source array; and intercepting the fourth plurality of kilovolt x-ray beams so that fan-shaped kilovolt x-ray beams emanate towards the object. The method includes receiving at the first detector, a first plurality of fan-shaped kilovolt x-ray beams from the first x-ray source array after the x-ray beams pass through the object and a second plurality of fan-shaped kilovolt x-ray beams from the second x-ray source array after the x-ray beams pass through the object. The first detector generates a first imaging signal for the received first plurality of fan-shaped kilovolt x-ray beams from the first x-ray source array and a second imaging signal for the received second plurality of fan-shaped kilovolt x-ray beams from the second x-ray source array. The method also includes receiving at the second detector, a third plurality of fan-shaped kilovolt x-ray beams from the first x-ray source after the x-ray beams pass through the object and a fourth plurality of fan-shaped kilovolt x-ray beams from the second x-ray source and after the x-ray beams pass through the object. The second detector generates a third imaging signal of the received third plurality of fan-shaped kilovolt x-ray beams from the first x-ray source and a fourth imaging signal from the received fourth plurality of fan-shaped kilovolt x-ray beams from the second x-ray source. The method also includes determining a stereoscopic image based on the first imaging signals for each of the first plurality of fan-shaped kilovolt x-ray beams from the first x-ray source and the second imaging signals for each of the second plurality of fan-shaped kilovolt x-ray beams from the second x-ray source, and 2) the third imaging signals for each of the third plurality of fan-shaped kilovolt x-ray beams from the first x-ray source and the fourth imaging signals for each of the fourth plurality of fan-shaped kilovolt x-ray beams from the second x-ray source. Finally, the method includes displaying the stereoscopic image (e.g., on a display).

In some examples, the radiation source includes an electronic portal imaging device in communication with the computer, where the first and second x-ray sources are positioned on either side of the electronic portal imaging device or where the first and second detectors are positioned on either side of the electronic portal imaging device. In some examples, the first and second x-ray source arrays are orthogonal to the first and second detector arrays. Each of the source and detector array pairs may generate a projection image.

In some implementations, the first and second x-ray source arrays include a kilovolt x-ray source. The therapy radiation source may generate a beam of x-rays having energy up to 25 MeV. The first, second, third and fourth pluralities of emitted kilovolt x-ray beams may share a central axis with the radiation beam. In some examples, none, one, or both of the first and third pluralities of kV x-ray beams are sequentially emitted from the first x-ray source and none, one, or both of the second and fourth pluralities of kV x-ray beams are sequentially emitted from the second x-ray source.

Another aspect of the disclosure provides a method of forming a CT image of an object being exposed to radiation therapy. The method includes rotating a first kV x-ray source array, a second kV x-ray source array, a MV x-ray radiation source, a first detector and a second detector array about an axis of rotation relative to the object, wherein the MV x-ray radiation source is positioned between the first and second detectors and emitting radiation beams; emitting a first plurality of KV x-ray beams from the first kV x-ray source array at different positions and intercepting the first plurality of kV x-ray beams so that fan-shaped x-ray beams emanate towards the object. The method also includes emitting a second plurality of kV x-ray beams from the second kV x-ray source array at different positions, and intercepting the second plurality of kV x-ray beams so that fan-shaped kV x-ray beams emanate towards the object. The method includes emitting a third plurality of kV x-ray beams from the first x-ray source array at different positions, and intercepting the third plurality of kV x-ray beams so that fan-shaped kV x-ray beams emanate towards the object. The method also includes emitting a fourth plurality of kV x-ray beams from the second x-ray source array at different positions, and intercepting the fourth plurality of kV x-ray beams so that fan-shaped kV x-ray beams emanate towards the object. In one embodiment, none, one or both of the first and third pluralities of kV x-ray beams are sequentially emitted from the first x-ray source and none, one, or both of the second and fourth pluralities of kV x-ray beams are sequentially emitted from the second x-ray source.

The MV radiation beams are emitted in a direction in-line with the plurality of the first or second emitted x-ray beams. The method includes receiving at a first detector a first plurality of fan-shaped x-ray beams from the first x-ray source array after they pass through the object and a second plurality of fan-shaped x-ray beams from the second x-ray source array after they pass through the object. The first detector generates a first imaging signal for the received first plurality of fan-shaped x-ray beams from the first x-ray source array and a second imaging signal for the received second plurality of fan-shaped x-ray beams from the second x-ray source array. The method also includes receiving at a second detector a third plurality of fan-shaped x-ray beams from the first x-ray source after they pass through the object and a fourth plurality of fan-shaped x-ray beams from the second x-ray source after they pass through the object that are received by the second detector. The second detector generates a third imaging signal for each of the received third plurality of fan-shaped x-ray beams from the first x-ray source and a fourth imaging signal from the received fourth plurality of fan-shaped x-ray beams from the second x-ray source. The method also includes determining a three-dimensional tetrahedron beam computed tomography image based on (1) the first imaging signals for each of the first plurality of fan-shaped x-ray beams from the first x-ray source and the second imaging signals for each of the second plurality of fan-shaped x-ray beams from the second x-ray source and (2) the third imaging signals for each of the third plurality of fan-shaped x-ray beams from the first x-ray source and the fourth imaging signals for each of the second plurality of fan-shaped x-ray beams from the second x-ray source. The rotation of the first x-ray source array, the second x-ray source array, the first detector and the second detector about the axis of rotation results in multiple imaging signals being reconstructed to generate a three-dimensional tetrahedron beam computed tomography image therefrom. The method also includes displaying the three-dimensional tetrahedron beam computed tomography image.

In some examples, the radiation source includes an electronic portal imaging device in communication with the computer, where the first and second x-ray sources are positioned on either side of the electronic portal imaging device or where the first and second detectors are positioned on either side of the electronic portal imaging device. In some examples, the first and second x-ray source arrays are orthogonal to the first and second detector arrays. Each of the source and detector array pairs may generate a projection image.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 16A is a front view of an exemplary imaging and radiation therapy system having a LINAC system that supports a dual source-dual detector tetrahedron beam computed tomography system.

Like reference symbols in the various drawings indicate like elements.

DETAILED DESCRIPTION

Figure 1:
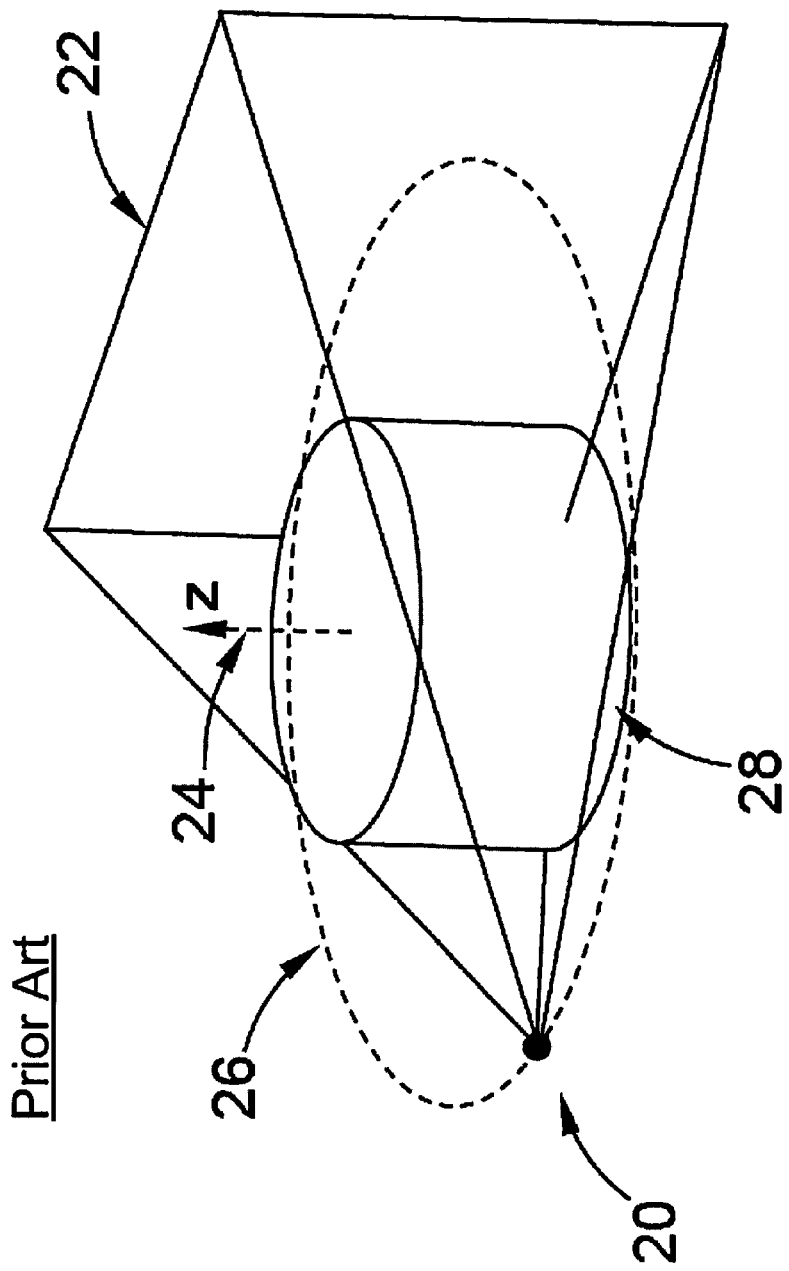
FIG. 1 is a schematic view of a prior art cone-beam computed tomography system.
Figure 2A:
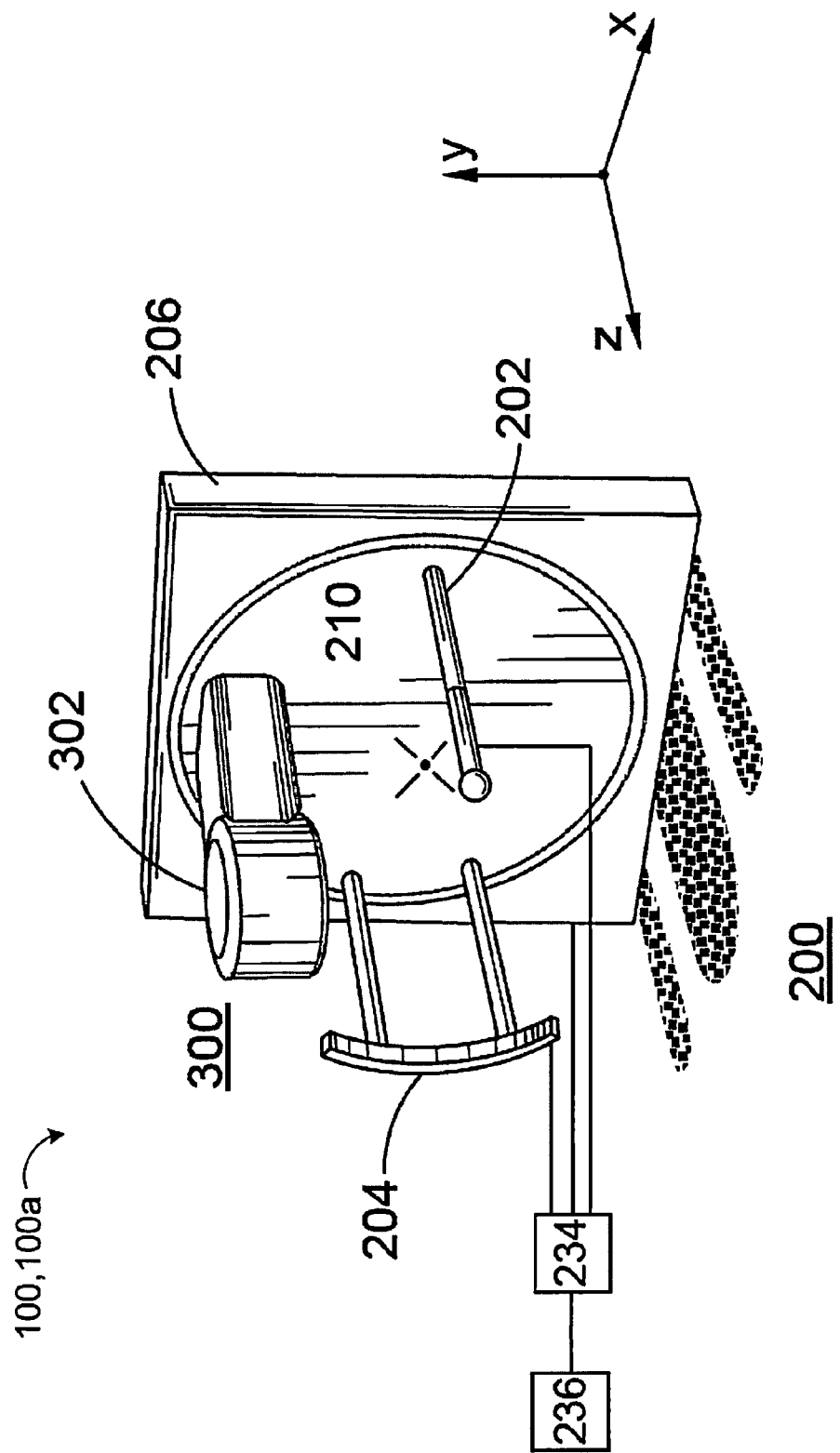
FIG. 2A is a schematic view of an exemplary a tetrahedron beam computed tomography system used in conjunction with a radiotherapy source in accordance with the present disclosure.
Figure 2B:
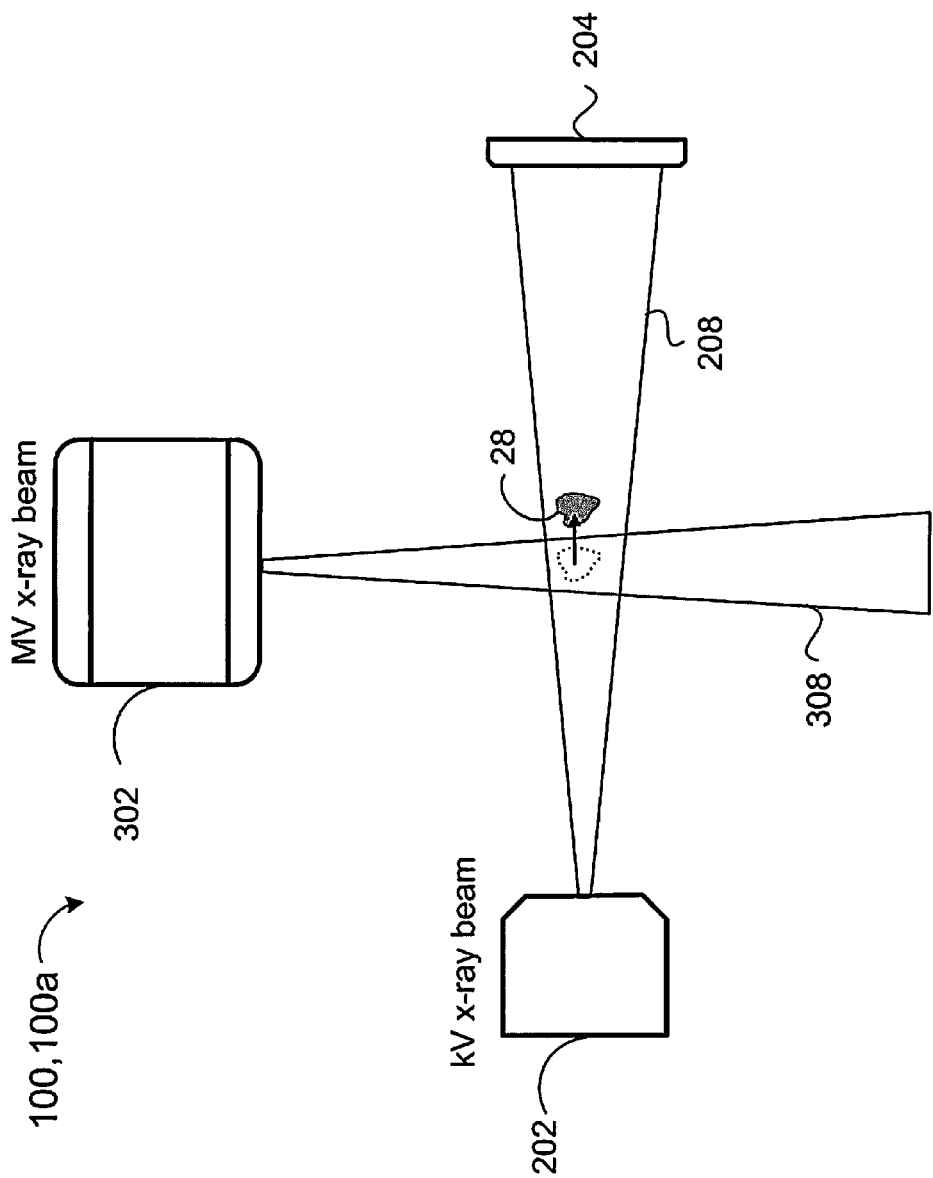
FIG. 2B is a schematic top view of an exemplary tetrahedron beam computed tomography system in conjunction with a radiotherapy source orthogonal to the tetrahedron beam computed tomography system.

Referring to FIGS. 2A and 2B an imaging and radiation therapy system 100 includes a wall-mounted tetrahedron beam computed tomography (TBCT) system 200 and a megavoltage radiotherapy system 300. The system 100 reduces the scatter generated in a volumetric computed tomography system, is compact, reduces the beam divergence in a transverse slice and reduces the lengths of detector arrays. The TBCT system 200 may be retrofitted onto an existing or new radiation therapy system 300 that includes a separate radiation therapy x-ray source. The wall-mounted TBCT system 200 includes a separate radiation therapy x-ray source, such as a linear accelerator 302, which is separately mounted to the rotating drum 210 of the TBCT. The linear accelerator 302 operates at a power level higher than that of the x-ray source 202 so as to allow for treatment of a target volume in a patient lying on movable table (not shown). The table is movable in the x, y and z-directions shown in FIG. 2A via a computer 234 having a display 236. In some examples, the computer 234 allows a user to determine the position of the table. The linear accelerator 302 generates a beam of radiation, such as photons or electrons, which have an energy up to 25 MeV. In some examples, the linear accelerator 302 is a linear particle accelerator (LINAC) that greatly increases the energy of charged particles.

The TBCT system 200 is a volumetric imaging system designed to overcome problems of cone beam computed tomography (CBCT) and to reconstruct a three-dimensional volume in a single gantry rotation. The TBCT system 200 includes an x-ray source array 202 and a multi-row imager/ detector 204 having a curved shape mounted on a gantry 206. In particular, the x-ray source array 202 is preferably a linear array of the x-ray source 202 and the multi-row detector is preferably a discrete scintillator/photodiode detector array. The detector array may be constructed from photodiode/scintillator array modules with data acquisition units, which are well known in the art. As shown in FIGS. 2A and 2B, x-ray beams (of the TBCT system 200) are produced by a linear array 202 of kilovoltage (kV) x-ray sources and are collimated into a stack of fan beams 208 directed towards a CT detector array 204 that is positioned orthogonally (as shown in FIG. 2A) to the kV x-ray source array 202. In contrast to the cone (pyramid) shaped volume formed by the point source and FPI in CBCT, the stacked fan beams 208 of TBCT form a tetrahedral volume. Most scattered photons are deflected out of the path of the fan beams and therefore go undetected. In addition to scatter rejection, the TBCT system 200 allows for the use of a high quality CT detector 204 similar to those used in helical CT scanners and thus improves online volumetric imaging.

As shown in FIGS. 2A and 2B, the detector 204 may be mounted to the face of a flat, circular, rotatable drum 210 of the gantry 206 of a medical linear accelerator 302. The imaging and radiation therapy system 100a of FIGS. 2A and 2B show the x-ray source 202 and detector array 204 mounted on the rotating drum 210 and arranged to be aligned perpendicular to (source 202) and within (array 204) the rotation plane defined by the drum 210. An example of mounting of an x-ray source and an imager to a rotatable drum is described in U.S. Pat. No. 6,842,502, the entire contents of which are incorporated herein by reference. In other examples, the imaging and radiation therapy system 100b shown in FIGS. 13-22, the x-ray source 1102 and the detector array 1104 are arrange to be aligned perpendicular to (source array 1102) and parallel to (detector array 1104) the rotation plane. In the examples shown in FIGS. 13-22, the treatment radiation beams 1008 are emitted in a direction in-line with the imaging kilovolt x-ray beams 1108.

Figure 3A:
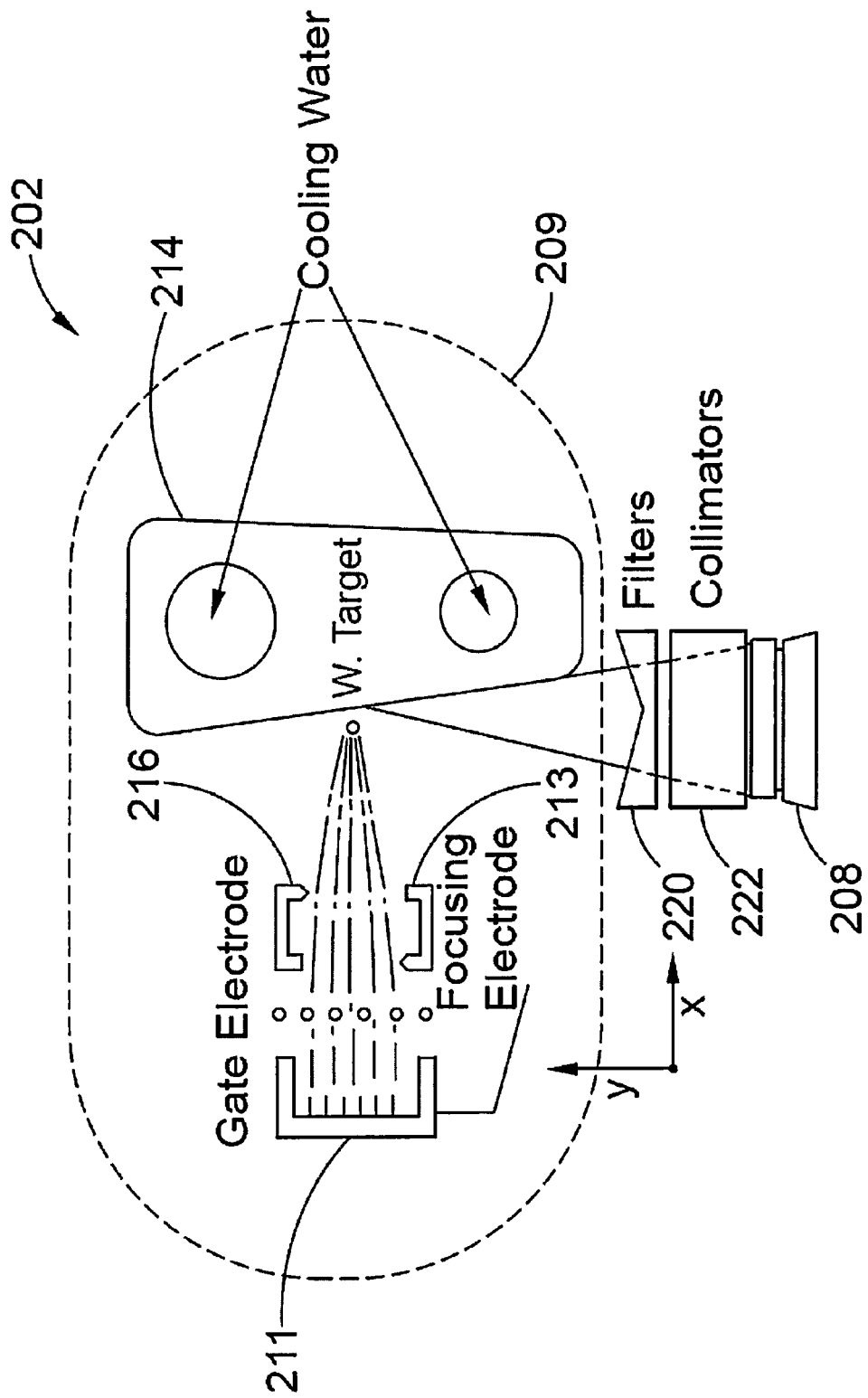
FIG. 3A is a side cross-sectional view of an exemplary a x-ray source array to be used with the tetrahedron beam computed tomography system of FIG. 6 in accordance with the present disclosure.
Figure 3B:
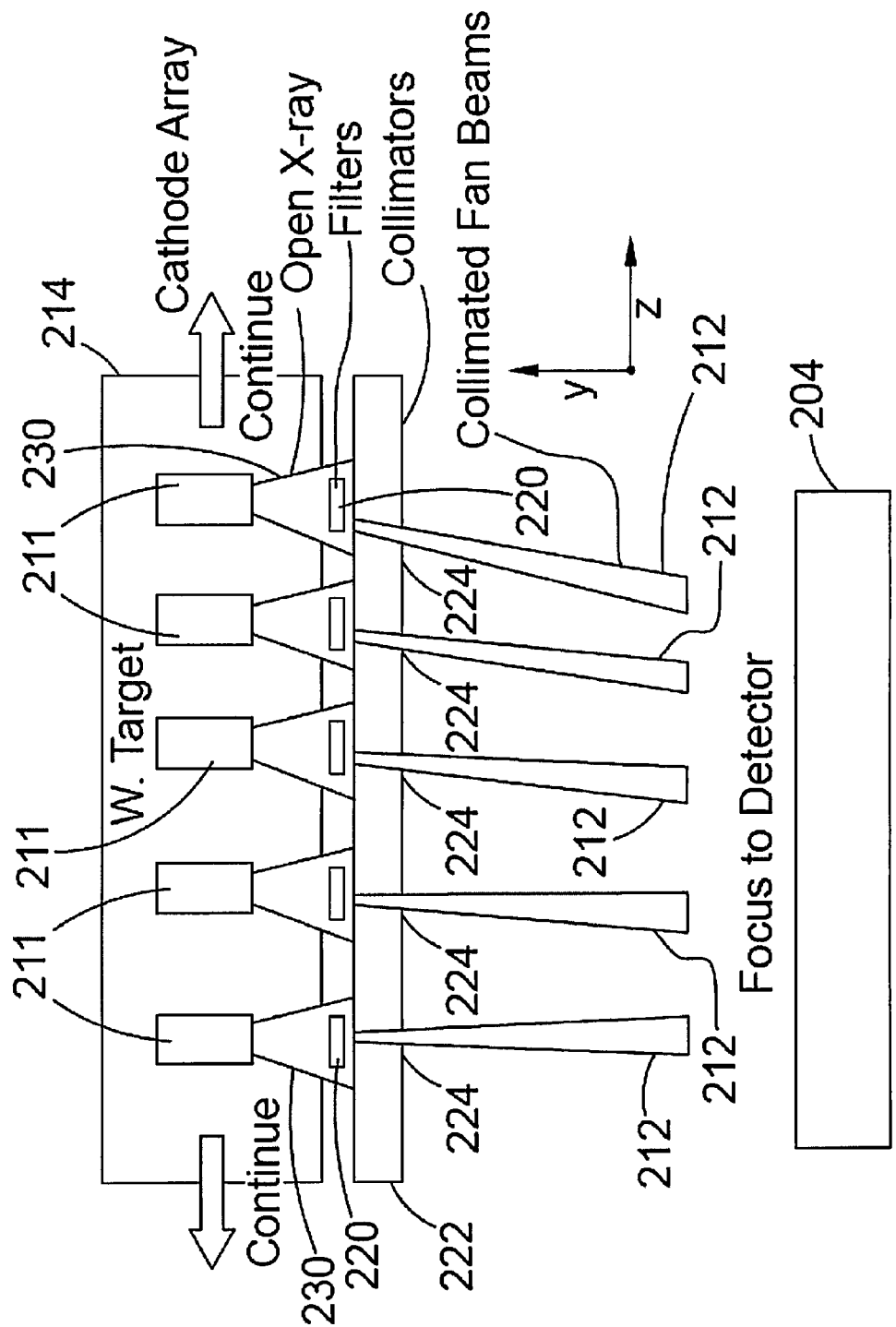
FIG. 3B is a front cross-sectional view of the exemplary x-ray source array of FIG. 3A.

As shown in FIGS. 3A and 3B, the x-ray source array 202 includes a single, cylindrical-like vacuum chamber 209 within a vacuum pressure. Possible materials for the vacuum chamber are glass, stainless steel, copper and aluminum. A plurality of cathodes, such as thermionic cathodes 211, are equally spaced from one another.

In operation, electrons are generated from the cathode 211 by the potential $V_g$ applied between the gate electrode 213 and the cathode 211. The electrons are accelerated by potential $V_a$, and focused into a small focus spot by potential $V_f$ and focusing electrodes 216. X-ray photons are generated via the bremsstrahlung effect when electrons strike on the molybdenum or tungsten anode target 214 and have an energy of about 80-140 keV when imaging a human body. The focusing electrodes 216 direct the electrons to different portions of the anode target 214 that represent focus spots that generate individual x-ray beams. In some examples, an x-ray source array 202 may be formed by scanning a single electron beam emitted from a single cathode.

As shown in FIGS. 3A and 3B, the x-ray source array 202 includes a single anode 214 and a plurality of the cathodes 211, wherein each cathode 211 or gate is controlled by a controller, such as MOSFET switches (not shown).

Figure 4A:
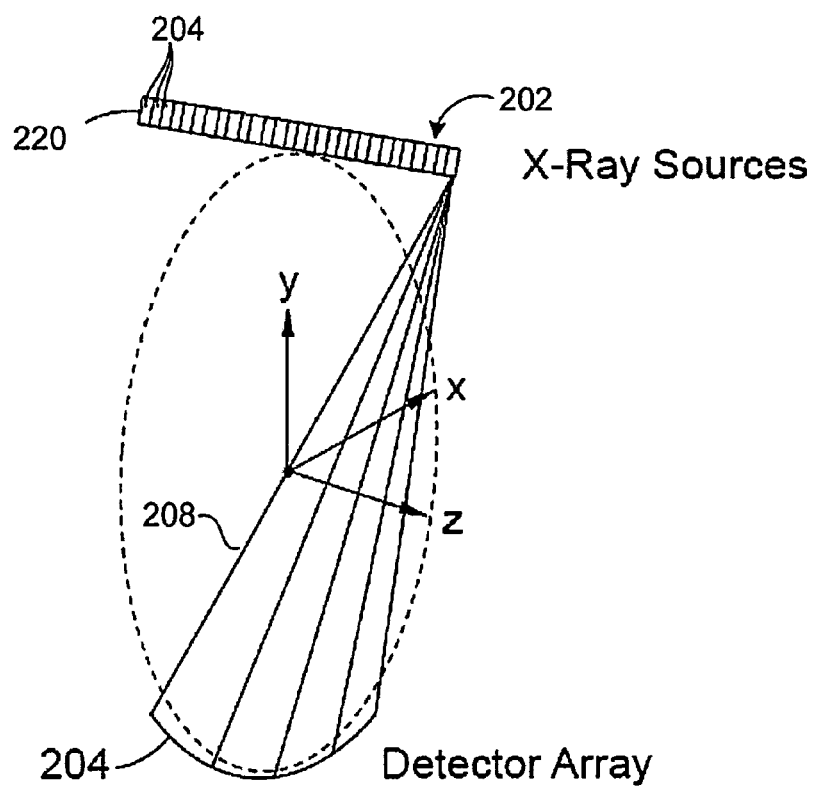
FIGS. 4A and 4B are schematic views of and exemplary configuration using a linear x-ray source array and curved slot collimator with the systems of FIGS. 2A-3B.
Figure 4B:
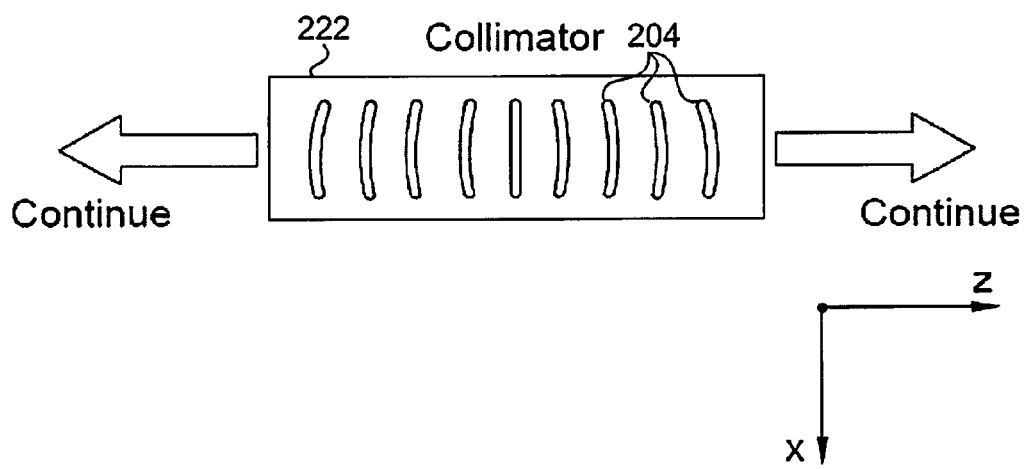

As described in U.S. Pat. No. 7,760,849, x-ray sources are sequentially switched on and off at a rate of approximately a few hundred Hz during a scan. As shown in FIGS. 3B, 4A, and 4B, the electrons emanating from each cathode 211 strike a different portion of the anode 214 and so a plurality of x-ray beams 230 are formed sequentially at different positions along the z-axis. The x-ray beams 230 pass through corresponding filters 220 and a stationary (relative to the x-ray source 202) collimator 222. The collimator 222 defines slots 224, which correspond to the cathodes 211. The slots 224 may be rectangular in shape with a width less than that of the beams 230 so that fan beams 212 are formed and which are directed to the detector 204, as shown in FIGS. 2 and 3B. With the sequential switching on and off of the source, a fan shaped beam sweeps across the object 28 to be imaged. During this process, the gantry 210 slowly rotates around the patient so that a plurality of two-dimensional images are captured that may be used to reconstruct a three-dimensional tetrahedron beam computed tomography image using a computer algorithm.

The examples described above can be implemented in various cone (wide) beam computed tomography systems, including on-board cone-beam computed tomography radiotherapy units, multi-row detector helical computed tomography systems, multi-row detector axial computed tomography systems, and C-arm flat panel cone-beam computed tomography systems, as well as other conventional diagnostic computed tomography systems. The applications of tetrahedron beam computed tomography may be employed in other forms of image guided interventions, such as image-guided surgery/biopsy with C-arm cone-beam computed tomography. The scatter rejection mechanism of tetrahedron beam computed tomography is also applicable to multi-row helical scanners and digital tomosynthesis.

Figure 5:
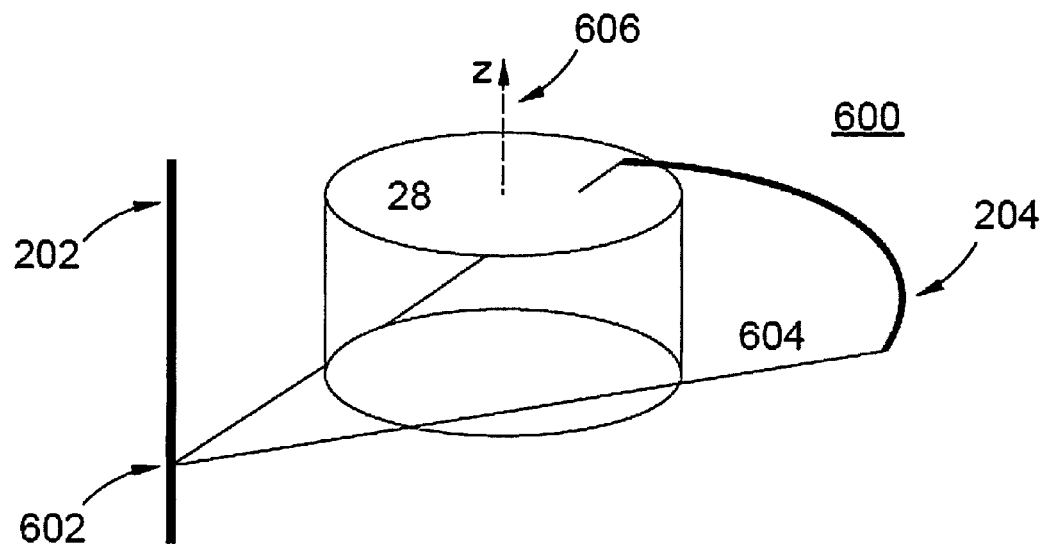
FIG. 5 is a schematic view of an exemplary tetrahedron beam computed tomography system.
Figure 6:
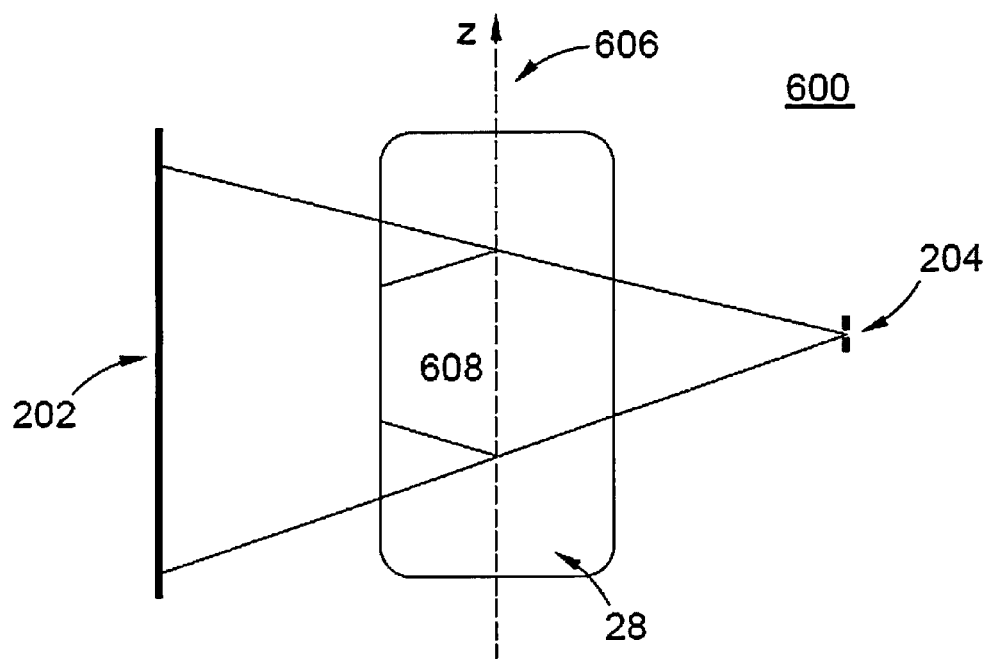
FIG. 6 is a cross-sectional view of the exemplary tetrahedron computed tomography system of FIG. 5.

A tetrahedron beam computed tomography system 600 that employs the components described previously with respect to FIGS. 2, 3A, 3B 4A and 4B is schematically shown in FIGS. 5 and 6. In particular, FIG. 5 illustrates the geometry of a tetrahedron beam computed tomography system 600. The system 600 includes an array of x-ray sources 202 and an array of x-ray detectors 204 that rotate about an axis 606. Such rotation may be accomplished by having the x-ray source arrays 202 and x-ray detector arrays 204 mounted on a rotating drum 210 of gantry 206.

The source array 202 and detector array 204 are orthogonal to each other. Both source array 202 and detector array 204 may be straight or curved. Each individual source 602 generates an x-ray beam, which is collimated to a fan-shaped beam 604 by a multi-slot collimator 222 (not shown). The array of sources 202 generates fan beams at different angles, which are received by the same detector 204. Similar to cone-beam computed tomography, a volumetric image may be reconstructed by tetrahedron beam computed tomography with a single rotation. But different from cone-beam computed tomography, the detector array 204 of tetrahedron beam computed tomography receives much less scatter photons due to the fan beam geometry. Consequently, tetrahedron beam computed tomography image quality and imaging dose are significantly improved.

Now referring to FIG. 6, after a rotation about the axis 606, both tetrahedron beam computed tomography and cone beam computed tomography are able to reconstruct the shaded volume 608. Due to the beam divergence, the source array 202 needs to be about twice as large as the shaded area. For example, in order to achieve 20 cm field of view in z dimension, the source array 202 needs to be about 40 cm long. Longer source array 202 is more expensive to build and less convenient to mount on the gantry 206. Besides the longer tube, the other problem of beam divergence is that the actual volume irradiated is larger than the volume 608. Some regions of the imaged subject 28 receives radiation but cannot be imaged.

Figure 7:
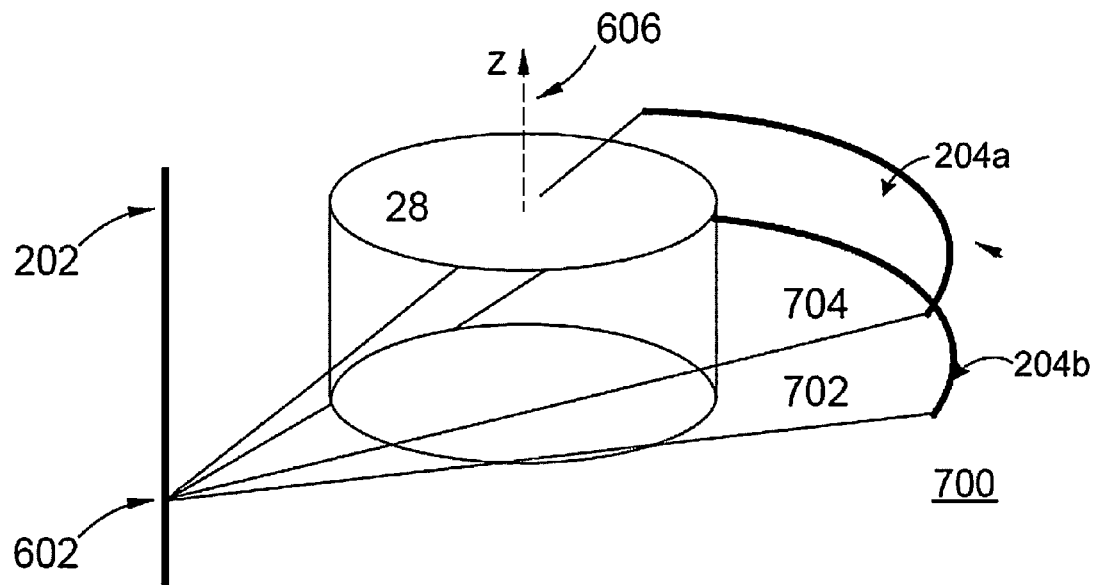
FIG. 7 is a schematic view of an exemplary tetrahedron beam computed tomography system in accordance with the present disclosure.
Figure 8:
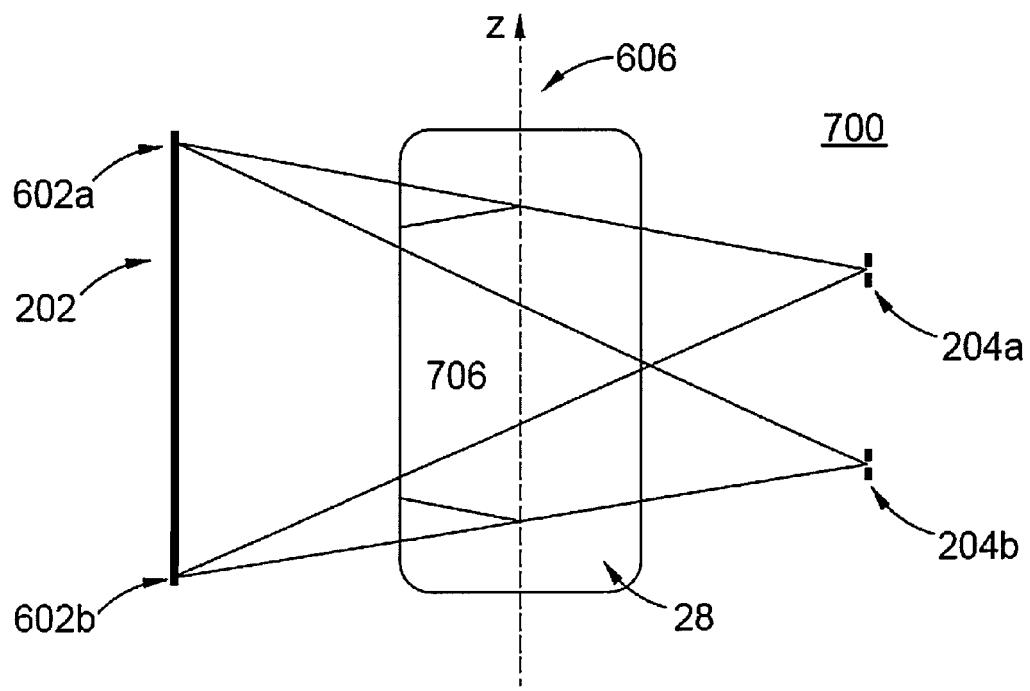
FIG. 8 is a cross-sectional view of the tetrahedron computed tomography system of FIG. 7.

FIG. 7 shows a tetrahedron beam computed tomography system 700 with two detector arrays 204a and 204b. The two detector arrays 204a and 204b are offset from the central plane that bisects the source array 202 and is perpendicular to the axis 606. Each x-ray individual source 602 of source array 202 forms two fan beams 702 and 704, which are received by the two detector arrays 204a and 204b, respectively. The fan beams may be received by one of or both of detector arrays 204a and 204b. Or different x-ray beams may be collimated to one of the two detector arrays 204a and 204b, alternatively. The source array 202 forms a tetrahedral volume with each of the detector arrays 204a and 204b. FIG. 8 is a lateral view of the tetrahedron beam computed tomography system 700, wherein sources 602a and 602b are the two outermost sources on the source array 202. As shown in FIG. 8, the reconstructed volume 706 of the tetrahedron beam computed tomography system 700 is much wider than the volume 608 of the tetrahedron beam computed tomography system 600 of FIG. 6. There may still be divergence but the angle is much smaller than that shown in FIG. 6. In some examples, the source array 202 is a linear multi-beam x-ray source and each detector array 204a and 204b is a discrete scintillator/photodiode detector array 204. The detector array 204 may be constructed from photodiode/scintillator array modules with data acquisition units, which are well known in the art.

Figure 9:
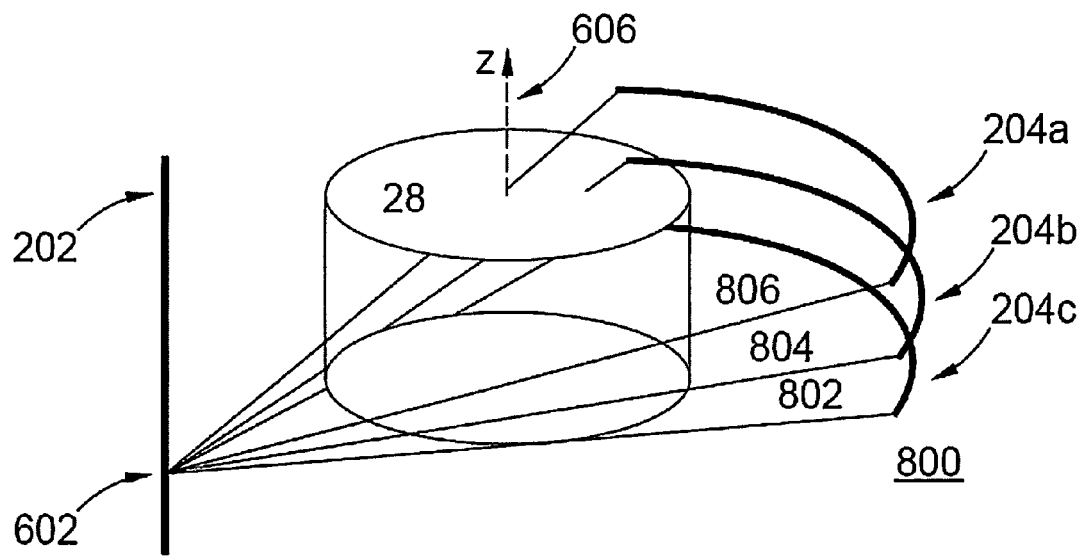
FIG. 9 is a schematic view of an exemplary tetrahedron beam computed tomography system.
Figure 10:
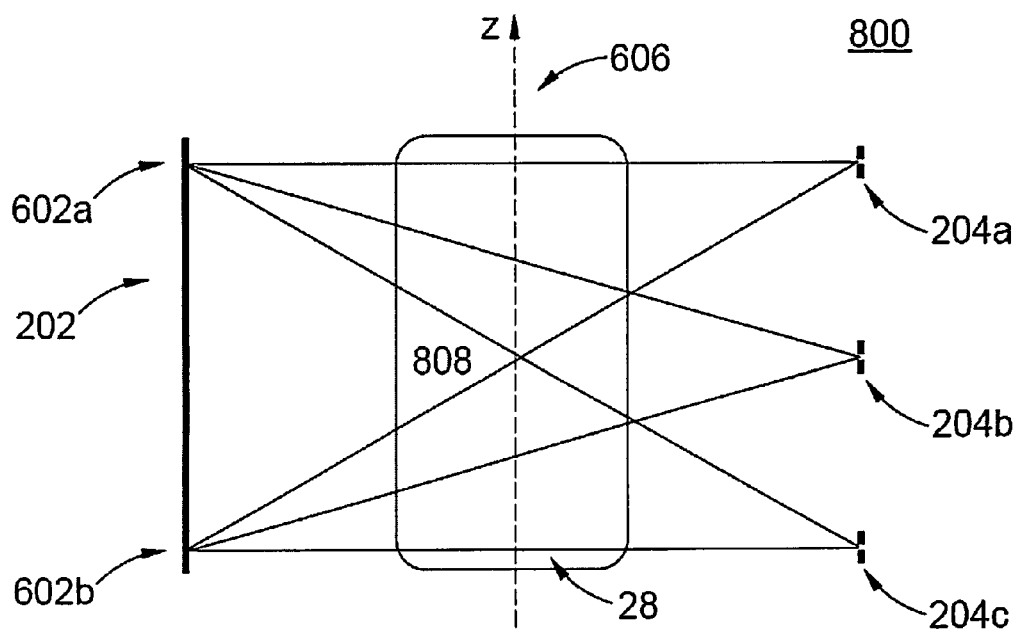
FIG. 10 is a cross-sectional view of the tetrahedron computed tomography system of FIG. 9.

Similarly, three detector arrays 204 can further reduce or eliminate the beam divergence. FIG. 9 shows a tetrahedron beam computed tomography system 800 with three detector arrays 204. One detector array 204b is located in the central plane and the other detector arrays 204a and 204c are offset from the central plane that bisects the source array 202 and is perpendicular to the axis 606. The source array 202 generates three fan beams 806, 804 and 802 that pass through the object 28 and are received by detector arrays 204a, 204b and 204c, respectively. The fan beams may be received by one of, two of or all three of the detector arrays 204a, 204b and 204c. The source array 202 forms one tetrahedral volume with each detector array 204. As shown in FIG. 10, the divergence of the x-ray beams may be totally eliminated in this configuration. In particular, the volume 808 that may be reconstructed is the same as the length of the x-ray source array 202. Hence a much shorter x-ray source array 202 is needed. For example, a 20 cm long source array 202 can reconstruct 20 cm field of view in the axial (z) dimension.

In some implementations, the curved detector arrays 204 of the systems 700 and 800 of FIGS. 7-10, have a radius of curvature that is centered about the longitudinal axis of the source array 202. With multiple detector arrays 204, the beam divergence in z direction is greatly reduced. The source array 202 is equal or slightly larger than the field of view in z direction. However, the beam divergence in the transverse plane remains the same. The lengths of the detector arrays 204 are about double the field of view in the transverse plane. For example if a 50 cm field of view is needed in the transverse plane, the detector length would be 80-100 cm depending on the ratio of the source-axis to detector-axis distance.

As described above, the systems 700 and 800 operate by having the source and detector arrays 202, 204 rotate about the axis 606 and acquiring and processing image data in a manner similar to that described in U.S. Pat. No. 7,760,849. Reconstruction of the image data may be done by using a CT reconstruction algorithm or a digital tomosynthesis algorithm in a well-known manner. The systems 700 and 800 can achieve rotation of the x-ray sources 202 and x-ray detectors 204 by having them mounted on a rotating drum 210 of the gantry 206 of FIG. 2 or implemented on a C-arm gantry, robotic arm gantry or closed ring gantry, movable C-arm of a stationary or mobile x-ray imaging device. Note that axial scans of the object 28 (object stationary) or helical scans of the object 28 (object moves to generate helical scan) may be performed. In addition, full, multiple and partial rotations of the sources and detectors may be performed. The three-dimensional data is shown on a display, 236 (e.g., e.g., a CRT (cathode ray tube), LCD (liquid crystal display) monitor, or touch screen for displaying information to the user and optionally a keyboard and a pointing device, e.g., a mouse or a trackball, by which the user can provide input to the computer) of the computing device 234.

Figure 11:
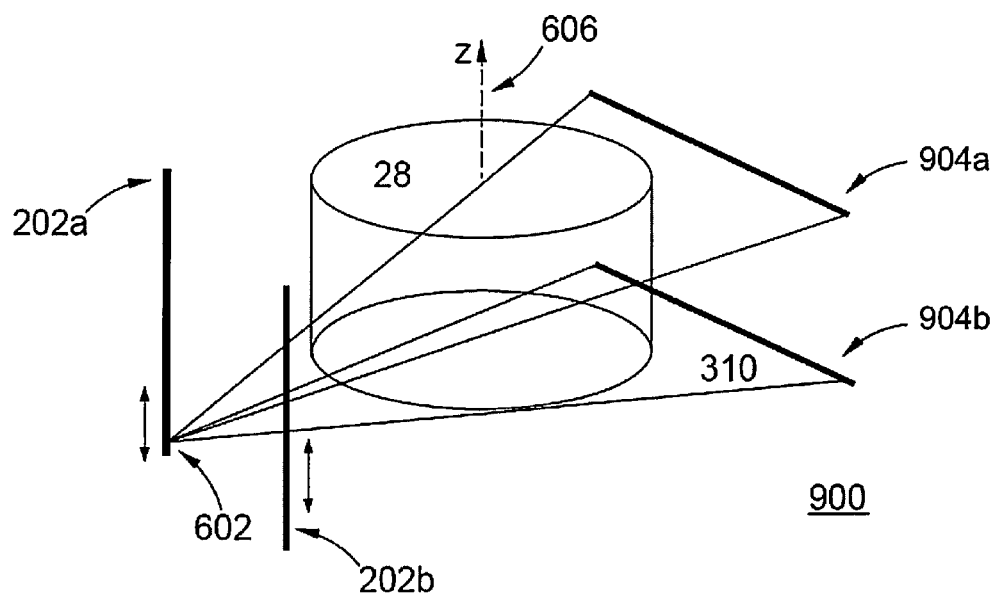
FIG. 11 is a schematic view of an exemplary tetrahedron beam computed tomography system.

In some implementations, multiple source arrays 202a and 202b may be used in a tetrahedron beam computed tomography system 900 as shown in FIG. 11. The source arrays 202 are parallel to the central axis 606, but positioned a distance offset from the central axis 606. Using multiple source arrays 202 can reduce beam divergence in the transverse plane. With reduced divergence, shorter detector arrays 204 may be used to achieve the same field of view in a transverse plane. In addition, the use of multiple detector arrays 902a and 902b offset from the central plane can allow for the use of shorter source arrays 202 and the reduction of beam divergence in the axial direction. At least two source arrays 202 are offset from the center so that the divergence in transverse plane is also reduced.

Figure 12:
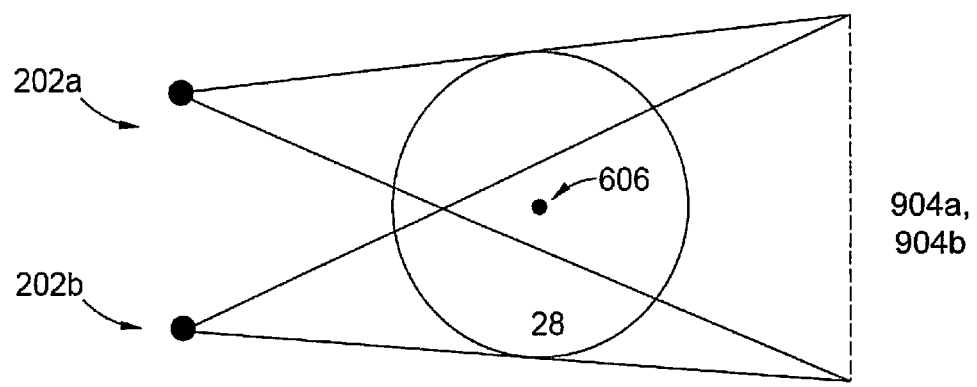
FIG. 12 is a cross-sectional view of the tetrahedron beam computed tomography system of FIG. 11.

As shown in FIG. 12, the two source arrays 202a and 202b are offset from the central axis 606. The divergence of the beams is smaller. Hence much shorter detector arrays 904a and 904b can cover the field of view of object 28. Because the detector arrays 904a and 904b are so short, it is unnecessary to use curved detectors. Both detector arrays 904a and 904b and source arrays 202a and 202b may be straight.

One advantage of TBCT system 900 is increased field of view. For example, in order to achieve the same field of view, the length of the linear source array 202 and detector array 204 may be reduced by half. Another advantage of the system 900 is that only the volume that may be reconstructed will be irradiated. With shorter sources and detectors, the TBCT system may be much more compact and suitable for use as mobile CT scanners. The system 900 also produces diagnostic quality images due to scatter rejection and the use of high quality detectors.

In some implementations, the detector arrays 904 of the system 900 of FIGS. 11 and 12, are spaced apart from one another by a certain distance and the sources are spaced apart from one another by a certain distance, wherein the distances depend on the particular geometry being used. In addition, the concept of the system 900 may be expanded to include sources and detectors that surpass two in number.

Note in the system 800 and 900, the beam from each source is unnecessary to be collimated to all detectors. They may be collimated to one or two detector arrays 904. With an increase in the field of view in the z-direction, the number of detector arrays 904 may surpass three.

Note that in each of the tetrahedron beam computed tomography systems illustrated in FIGS. 2-12, the detector array 204 forms a tetrahedron volume with the linear source array 202. Usually the requirement of field of view in z direction is much larger than field of view in transverse plane. For example, regular CT images may have 20 cm length in z direction and 50 cm field of view in transverse plane. In the systems 700, 800 and 900, it is preferable to have source array(s) 202 perpendicular to the rotation plane and detector arrays 204 parallel to the rotation planes. This is because it is easier to make a long detector array 204 than a long source array 202.

With the use of multiple source arrays 202 in the system 900, the length of the source arrays 202 and detector arrays 904 may be similar. In this case, it does not matter which one of the detector and source is parallel to the rotation axis. Hence the positions of source arrays 202 and detector arrays 204 shown in FIGS. 2-16 may be switched. In addition, the fan beams may be received by one of or both of detector arrays 904a and 904b.

As described above, the system 900 operates by having the source and detector arrays 202, 904 rotate about the axis 606 and acquiring and processing image data in a well-known manner. Reconstruction of the image data may be done by using a CT reconstruction algorithm or a digital tomosynthesis algorithm, wherein the latter has a lower image quality and is used when smaller angles of rotation of the sources and detectors are involved. Such rotation may be accomplished by having the x-ray sources 202 and x-ray detectors 904 mounted on a rotating drum 210 of the gantry 206 of the radiation treatment machine of FIG. 2 or implemented on a C-arm gantry, robotic arm gantry or closed ring gantry. Note that axial scans of the object 28 (object stationary) or helical scans of the object 28 (object moves to generate helical scan) may be performed. In addition, full, multiple and partial rotations of the sources and detectors may be performed. The three-dimensional data is shown on a display, 236.

The systems 700, 800 and 900 can have full rotation with the gantry or partial rotation. The rotation may be axial or helical depending on the image reconstruction algorithms. The data acquired by the system may be used for 3D CT image reconstruction or digital tomosynthesis image reconstruction.

In some implementations, the number of source arrays is more than two. Moreover, each detector may receive x-ray fan beams from one or more sources, i.e., each of the detectors does not have to receive x-ray fan beams from all sources.

Figure 13:
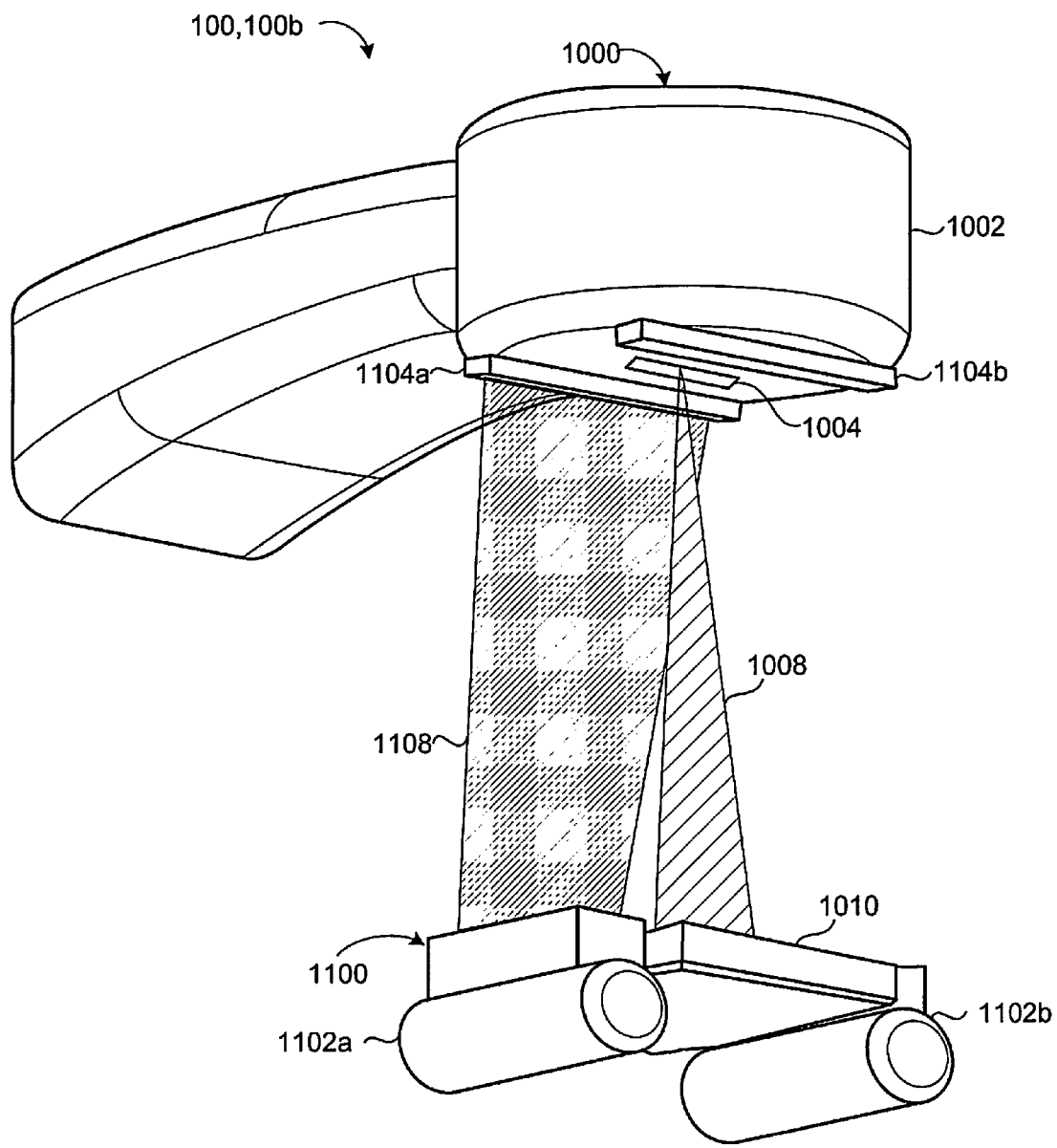
FIG. 13 is a schematic view of an exemplary imaging and radiation therapy system.
Figure 14:
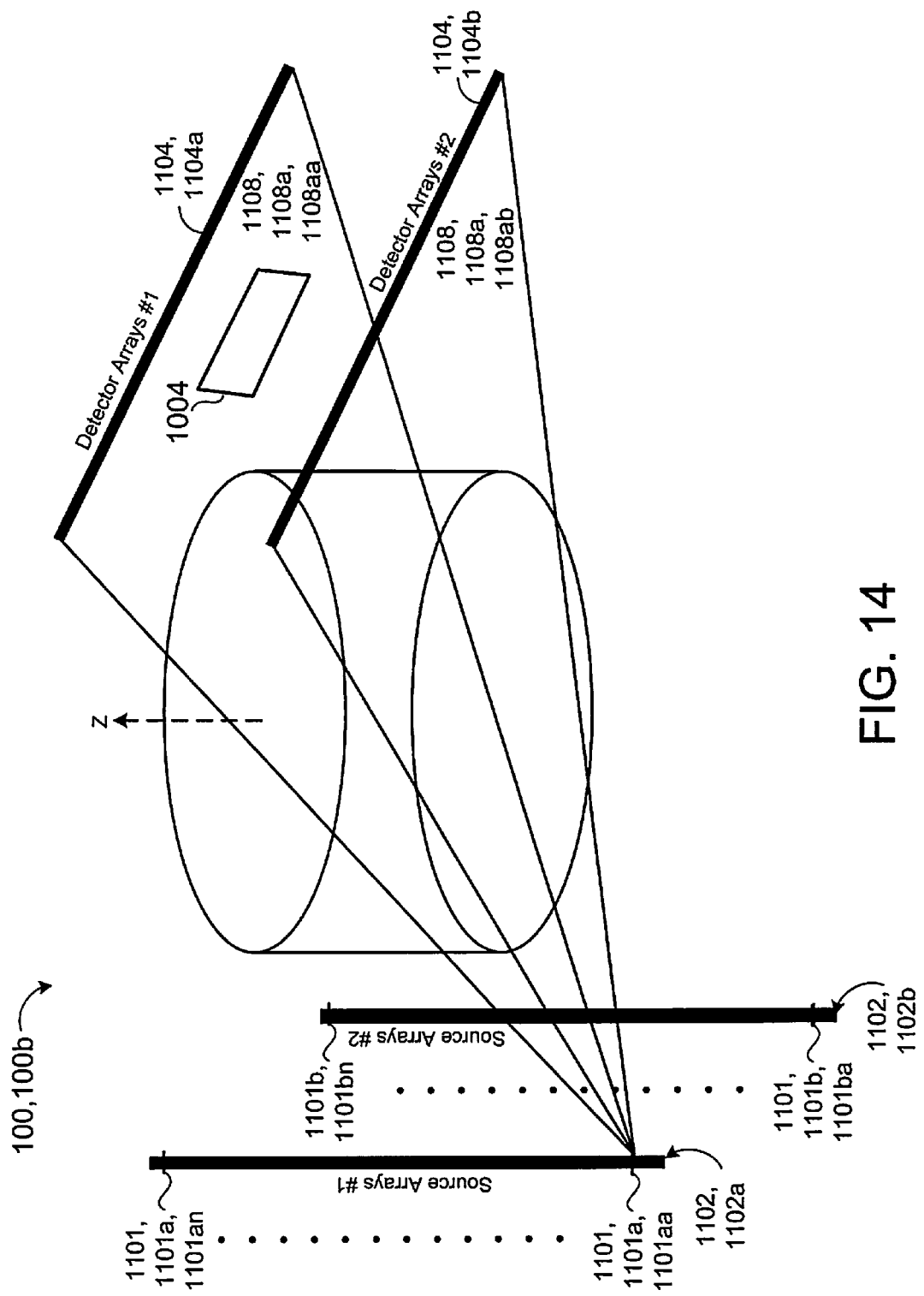
FIG. 14 is a schematic view of the exemplary imaging and radiation therapy system of FIG. 13.

Referring to FIGS. 13 and 14, a dual-source dual-detector TBCT and radiation therapy system 100b includes a TBCT system 1100 and a megavoltage radiotherapy system 1000. The megavoltage radiotherapy system 1000 includes a therapy radiation source 1004. As previously discussed, the geometry of a TBCT system is flexible and is not limited to the use of one detector array 1104 and one source array 1102; that is, two or more source arrays 1102 and/or two or more detector arrays 1104 may be employed for different situations. As shown, a dual source-dual detector TBCT system 1100, includes two source arrays 1102 and two detector arrays 1104. The dual source-dual detector TBCT system 1100 is capable of performing both volumetric CT imaging and real-time stereoscopic imaging. The geometry of the TBCT system 1100 may include two source arrays 1102a, 1102b and two detector arrays 1104a, 1104b. Incorporating two detector arrays 1104a, 1104b into the TBCT system 1100 reduces the axial convergence of the beams, subsequently reducing the cone angle and increasing the longitudinal field of view (FOV). Similarly, using multiple source arrays 1102a, 1102b can reduce the length of the detector arrays 1104a, 1104b that would be necessary to achieve the same transverse field of view (FOV) and, therefore, reduce the transverse divergence of the beams.

Figure 15:
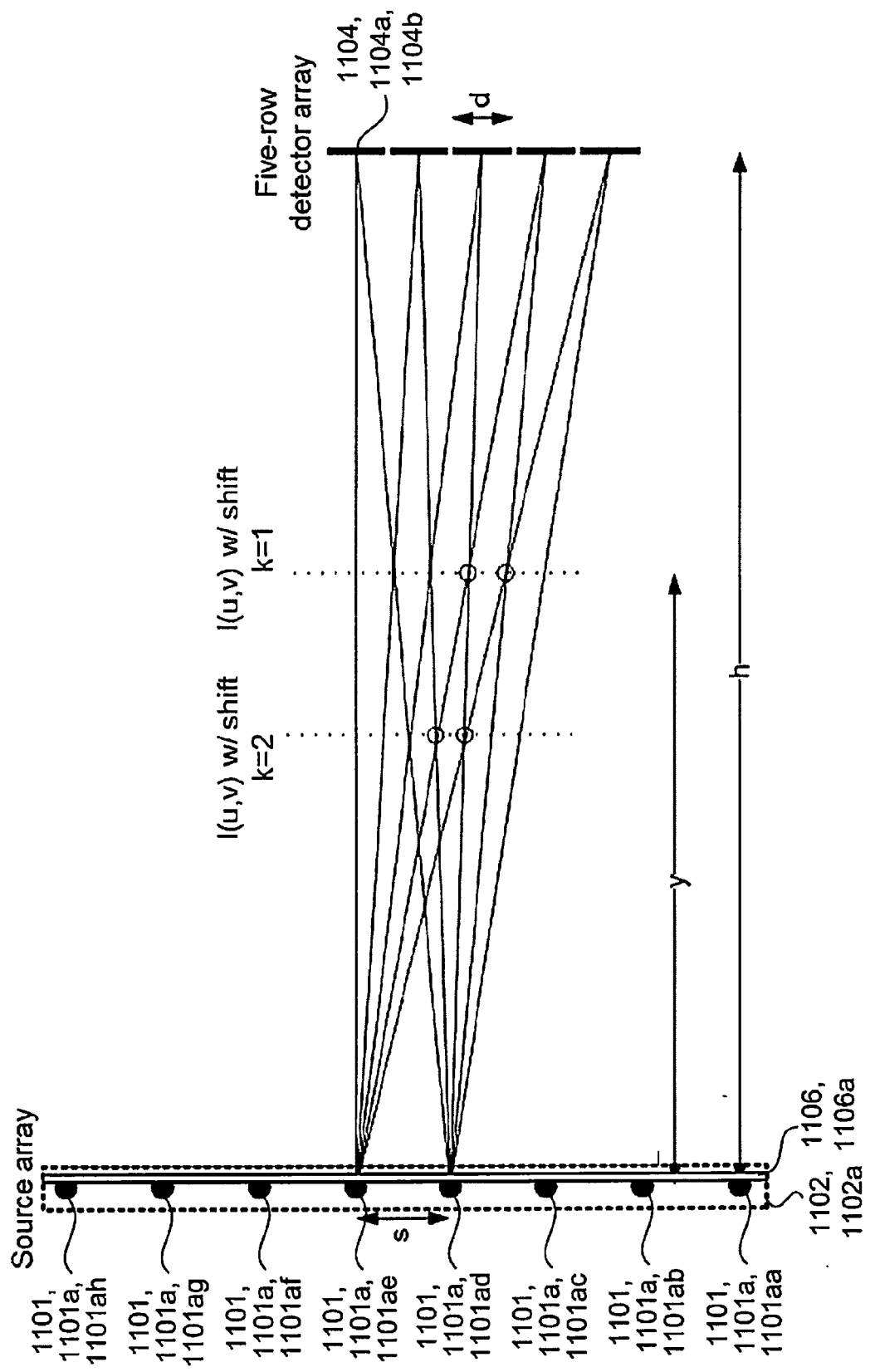
FIG. 15 is a schematic view of the exemplary imaging and radiation therapy system.

As shown in FIGS. 14 and 15, first and second source arrays 1102a and 1102b and detector arrays 1104a and 1104b are linearly orthogonal to each other. Both the source arrays 1102a and 1102b and the detector arrays 1104a and 1104b can be straight or curved. Each source array 1102 includes multiple sources 1101 (e.g., cathodes) that form a single row or multiple rows of sources 1101. Each individual source 1101 of the source array 1102 generates an X-ray beam which is collimated to a fan-shaped beam 1108 by a multi slot collimator 1106. Referring to the figures, the first and second source arrays 1102a, 1102b each include at least one x-ray source 1101. For example, the first array source 1102a includes x-ray sources 1101aa-1101an where each of sources 1101aa-1101an generates an x-ray beam 1108 First x-ray source 1101aa generates a first x-ray beam 1108a having a first portion 1108aa detected by the first detector 1104a and a second portion 1108ab detected by the second detector 1104b. The second array source 1102b includes x-ray sources 1101ba-1101bn where each of sources 1101ba-1101bn generates an x-ray beam 1108. First x-ray source 1101ba generates a first x-ray beam 1108b having a first portion 1108ba detected by the first detector 1104a and a second portion 1108bb detected by the second detector 1104b. Similarly, each source 1101 of the first or second source arrays 1102a, 1102b emits a beam 1108 that is detected by one or both the detector arrays 1104. The source 1101 generates an X-ray beam 1108 which is collimated to a fan-shaped beam 1108 by a multi-slot collimator 1106. Each array 1102 has a collimator 1106. The first source array 1102a generates fan beams 1108aa-1108an at different angles which are received by the detector arrays 1104a and 1104b. Source array 1102b also generates fan beams 1108ba and 1108bn at different angles which are received by the detector arrays 1104a and 1104b. Similar to cone-beam CT, a volumetric image can be reconstructed by tetrahedron beam computed tomography with a single rotation. However, the dual source-dual detector TBCT system 1100 provides a better image quality and imaging doses are significantly improved. In some examples, the x-ray sources 1101 of the x-ray source arrays 1102 may be turned on sequentially. Alternatively, the x-ray sources 1101 of the x-ray source arrays 1102 may be turned on simultaneously.

As shown in FIGS. 13-21, the dual source-dual detector TBCT system 1100 has a linear accelerator 1002 having a therapy radiation source 1004 in a location in-line between kV x-ray source arrays 1102a and 1102b. This reduces scatter generated in a volumetric computed tomography system and provides for a compact volumetric computed tomography system, in-line kV imaging, and real-time stereoscopic imaging, which provides three dimensional coordinates of markers. The linear accelerator 1002 operates at an energy level higher than that of x-ray source arrays 1102a and 1102b and generates a treatment beam of x-rays or particles 1008.

Now referring back to FIGS. 2A and 2B, geometric miss occurs when the treatment beam 308 from the linear accelerator 302 misses object 28 (i.e., a tumor) because the object 28 moves out of the treatment beam 308 (e.g., because the person moved). During a treatment, continuous kV x-ray images can be acquired to detect if the object 28 has moved out of the treatment field. An orthogonal configuration, as shown in FIGS. 2A and 2B, where the MV treatment beam 308 is orthogonal to the kV imaging beam 208 may not detect motion that is orthogonal to the treatment beam 308. However, referring to FIGS. 13 and 14, with an in-line configuration where the therapy radiation source 1004 is located between the detector arrays 1104a, 1104b (or the source arrays 1102a, 1102b) and the view of the x-ray images is in the direction of treatment beam 1008, the fan-shaped beams 1108a, 1108b from the source arrays 1102a, 1102b can be detected by detector arrays 1104a and 1104b and geometric miss may be avoided.

The dual-source dual-detector TBCT and radiation therapy system 100b (that includes the dual-source dual-detector TBCT system 1100 and megavoltage radiotherapy system 1000 shown in FIGS. 13 and 14 overcomes the problem of geometric miss because its central axis is open and allows for the placement of therapy radiation source 1004 of the linear accelerator 1002 between x-ray sources 1102a, 1102b, (or the detector arrays 1104a, 1104b) i.e., therapy radiation source 1004 is "in-line" with the x-ray sources 1102a, 1102b. The dual-source dual-detector TBCT system 1100 can share the same central axis as the treatment beam 1008 allowing for the location of the MV treatment between the source arrays 1102a, 1102b. The system 1100 can be conveniently installed on LINAC gantries without major modification to the gantries.

FIG. 13 shows the dual-source dual-detector TBCT system 1100 mounted on a regular LINAC gantry. The source arrays 1102a, 1102b are located beside an electronic portal imaging device (EPID) 1010 and below the head of the linear accelerator 1002. This arrangement allows the MV treatment beam 1008 to pass through the center of the system 1100. The EPID 1010 provides instantaneous radiographic imaging on a computer monitor.

In some implementations, the location of source arrays 1102a, 1102b may be switched with the location of detector arrays 1104a and 1104b. However, because of the radiation susceptibility of the detector arrays 1104a and 1104b and the dimensions of the x-ray tubes, in one embodiment, the detector arrays 1104a and 1104b are installed on the head of the linear accelerator 1002 (outside of the path of treatment beam 1008) and the x-ray source arrays 1102a and 1102b are installed alongside the EPID 1010.

Similar to cone-beam computed tomography, a volumetric image can be reconstructed by the dual-source dual-detector TBCT system 1100 with a single rotation. But different from cone-beam computed tomography, the detector arrays 1104a and 1104b of the dual-source dual-detector TBCT system 1100 receive much less scatter photons due to the fan beam geometry. Consequently, computed tomography image quality and imaging dose are significantly improved when using the dual-source dual-detector TBCT system 1100.

Referring to FIG. 15, in addition to producing volumetric CT images, the dual source-dual detector TBCT system 1100 can also perform 2D radiographic imaging similar to CBCT. In one embodiment, the individual x-ray sources 1101 (e.g., 1101a and 1101b) of the x-ray source arrays 1102a and 1102b are turned on and off sequentially. For a one-row detector array 1102a, each x-ray source 1101a produces a 1D projection $p_n$ as shown in equation 1, $$p_n = (p^1, \ldots, p^M) \in \mathbb{R} \quad (1)$$

where n is the source index and M is the number of detector columns. The 1-D projections from all sources 1101 can simply be stacked together to create a 2D radiographic image of dimension M×N, where N is the number of x-ray sources 1101. However, the number of x-ray sources 1101 may be limited. With this method, the radiographic image resolution in the z-direction is limited to about a few mm, which is insufficient for fluoroscopic imaging.

Multi-row CT detectors have high, isotropic spatial resolution. Modern solid-state CT multi-row detectors have a pixel size less than 1 mm. The dual-source dual-detector TBCT system 1100 uses the same detector used in helical CT scanners. Data from a multi-row detector array 1104 can be utilized to improve the image resolution along the z-axis (source array direction). As shown in FIG. 15, the beams 1108 from all x-ray pixels converge to the width of the multi-row detector array 1104, each individual beam 1108a and 1108b diverges to the width of the multi-row detector array 1104. Therefore, with a multi-row detector array 1104, the image resolution along the z-axis is determined by the size of the detector pixel and not the source spacing.

In some examples, the shift-and-add (SAA) method is used to combine all the data received by a data processing device (e.g., computer (not shown)). This method is similar to radiographic imaging with scanning-beam digital x-ray (SBDX). The SAA method is performed by using the source array in the z-direction because a one dimensional source array is used in the dual-source dual-detector TBCT system 1100. The detector length in the x-direction remains unchanged. The SAA method can render the anatomic features of the object 28 (e.g., organ or tumor) without blurring the image at a specific depth along the y-axis.

Each scan of an x-ray source array 1102 generates a projection data matrix P with dimensions of L×M×N, where L is the number of detector rows. In the SAA method, projection images from the x-ray sources 1101 are shifted by a multiple of the detector pixel size and then superimposed onto each other according to $$I_k(u, v) = \sum_{n=1}^{N} \sum_{l=1}^{L} W(v) P(l, m, n) \delta_{v,(nk+1)} \quad (2)$$

where $I_k(u, v)$ is the resulting 2-D radiographic projection image, k is the shift, l is the detector row index, m is the detector column index, n is the source index, and $\delta_{v,(nk+1)}$ is a Kronecker delta. Image index u and detector column m are the same since the SAA method is only performed in one dimension. In this forward projection method, each radiographic image row v has a different number of projections that contribute to it. Therefore, a weighting factor W(v) is used to weight the contributions of each image row in order to achieve a uniform intensity throughout the image. The shift k determines the depth y at which the anatomic features can be rendered without blurring. The depth y is calculated by equation 3:

$$y(k) = \frac{hs}{s+k} \quad (3)$$

where h is the source to detector distance, d is the detector pixel size, and s is the x-ray source spacing.

Figure 16B:
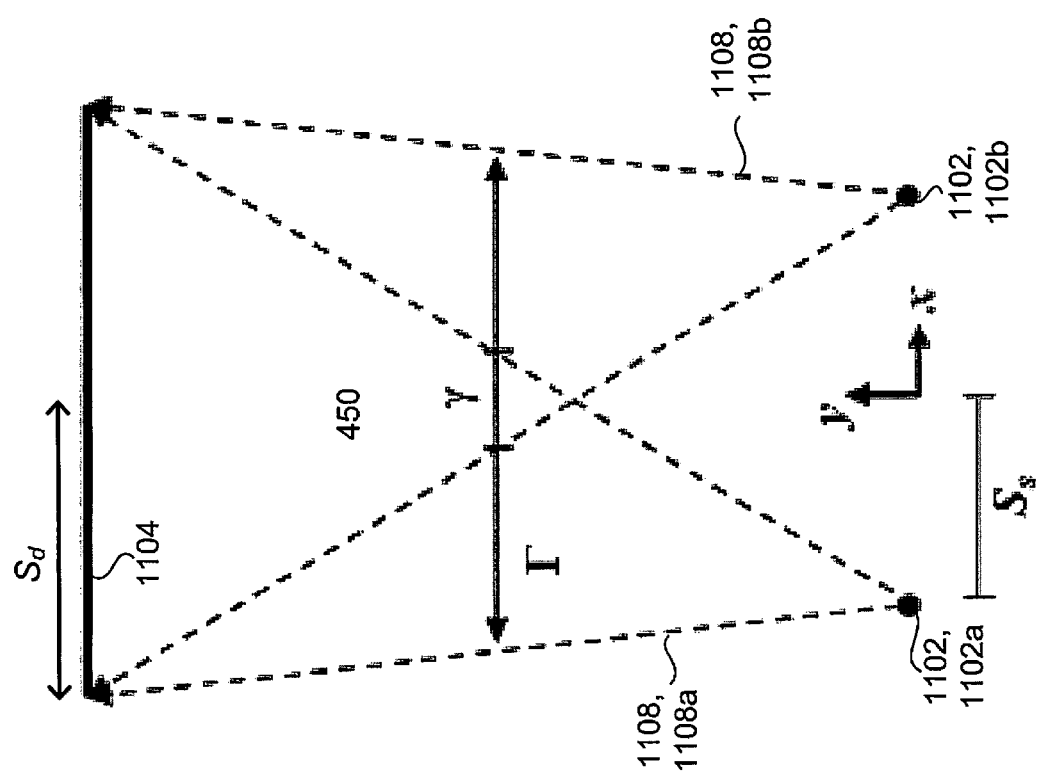
FIG. 16B is a schematic top view of the dual source-dual detector tetrahedron beam computed tomography system of FIG. 16A.
Figure 16C:
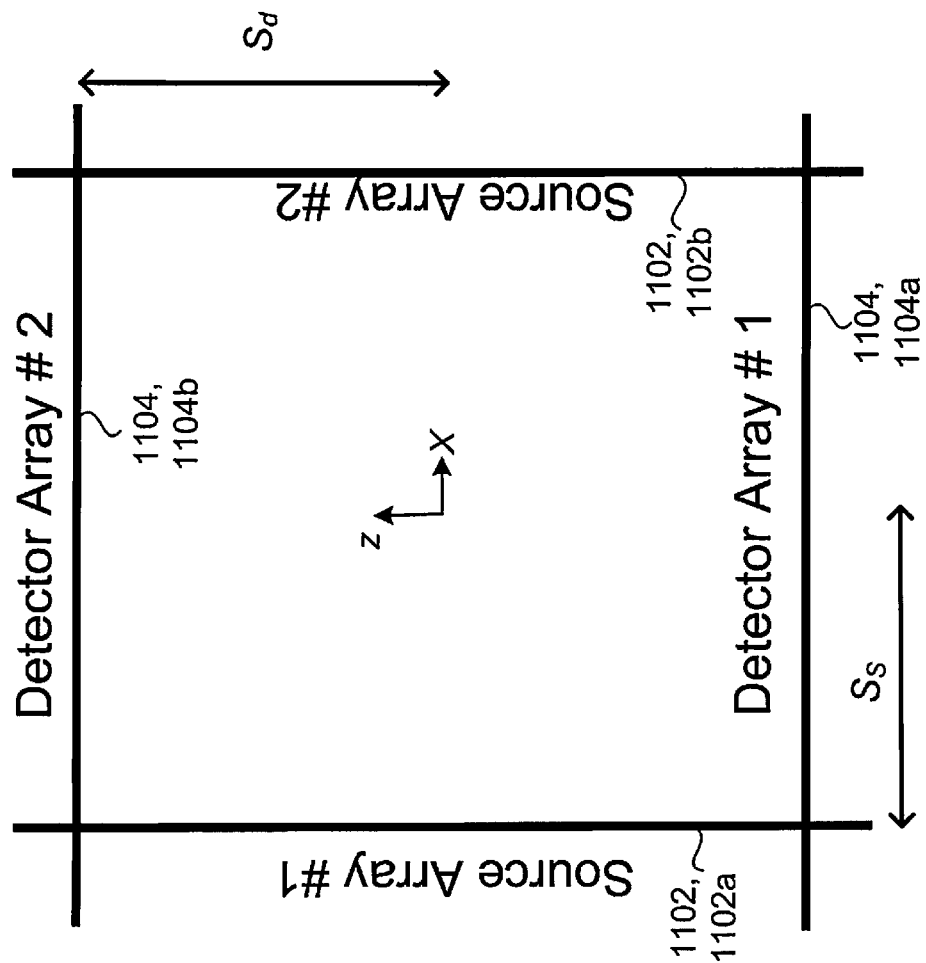
FIG. 16C is a schematic top view of the dual source-dual detector tetrahedron beam computed tomography system of FIG. 16A.

Referring to FIGS. 16A-16C, in some implementations, the dual source-dual detector TBCT system 1100 positioned on a LINAC gantry is shown. In one embodiment, the dual source-dual detector TBCT system 1100 produces four projection images corresponding to the beams from four source array-detector array pairs, e.g., source array 1 (1102a) is detected by detector array 1 (1104a) and detector array 2 (1104b), and source array 2 (1102b) is detected by detector array 1 (1104a) and detector array 2 (1104b). In some examples, the distance between the first and second detector arrays 1104a, 1104b is about 47 centimeters, and the distance between the first and second source arrays 1102a, 1102b is about 42 centimeters. As illustrated in the figures, none of the beams 1108 cover the full FOV (field of view). Instead, the beams 1108 overlap only in a small region 1150 at the center of the FOV. Stereoscopic imaging can be performed only in this overlapped small region. In this implementation, the configuration as shown in FIG. 16B provides a stereoscopic FOV, δ, of approximately 10 cm and a CT reconstruction FOV, Γ, of 45 cm. The stereoscopic FOV can be increased if a smaller FPI for portal imaging is chosen.

In some examples, pixel coordinates of anatomic features or fiducial markers can be determined in projection images either manually or automatically using computer algorithms, the spatial coordinates of the markers can be obtained by the below equation:

$$x = S_S\left(\frac{u_2 - u_1}{2S_S + u_1 + u_2}\right), \quad (4)$$

$$y = h\left(\frac{x + S_S}{S_S + u_2}\right),$$

$$z = -S_d + (S_d + v_1)\left(1 - \frac{y}{h}\right)$$

where x, y, z are the spatial coordinates of the marker, h is the source to detector distance, $S_S$ is the distance of the source arrays 1102a, 1102b to the central axis, and $S_d$ is the distance of the detector arrays 1104a, 1104b to the central axis. $u_i$ and $v_i$ are the pixel coordinates of the markers in the projection image i.

Figure 17A:
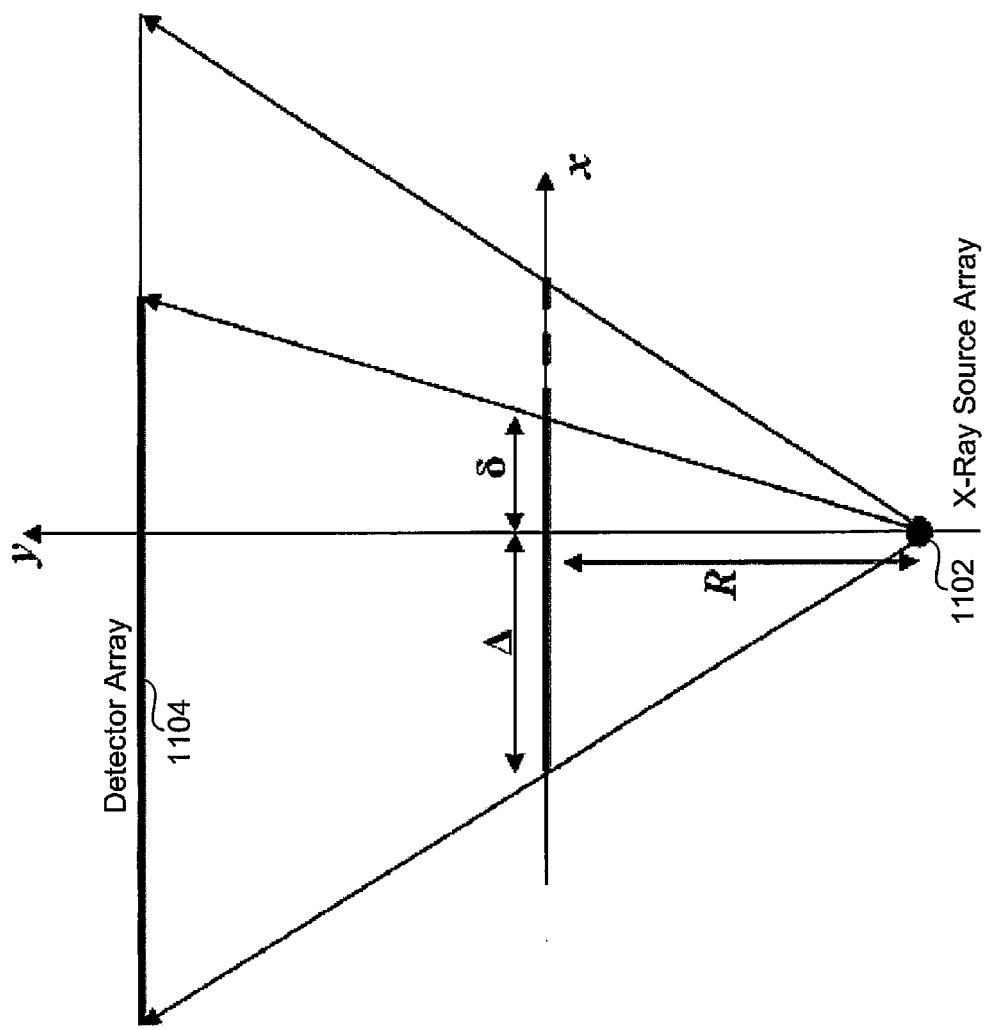
FIG. 17A is a schematic view of the geometry of a CT system with a displaced detector.
Figure 17B:
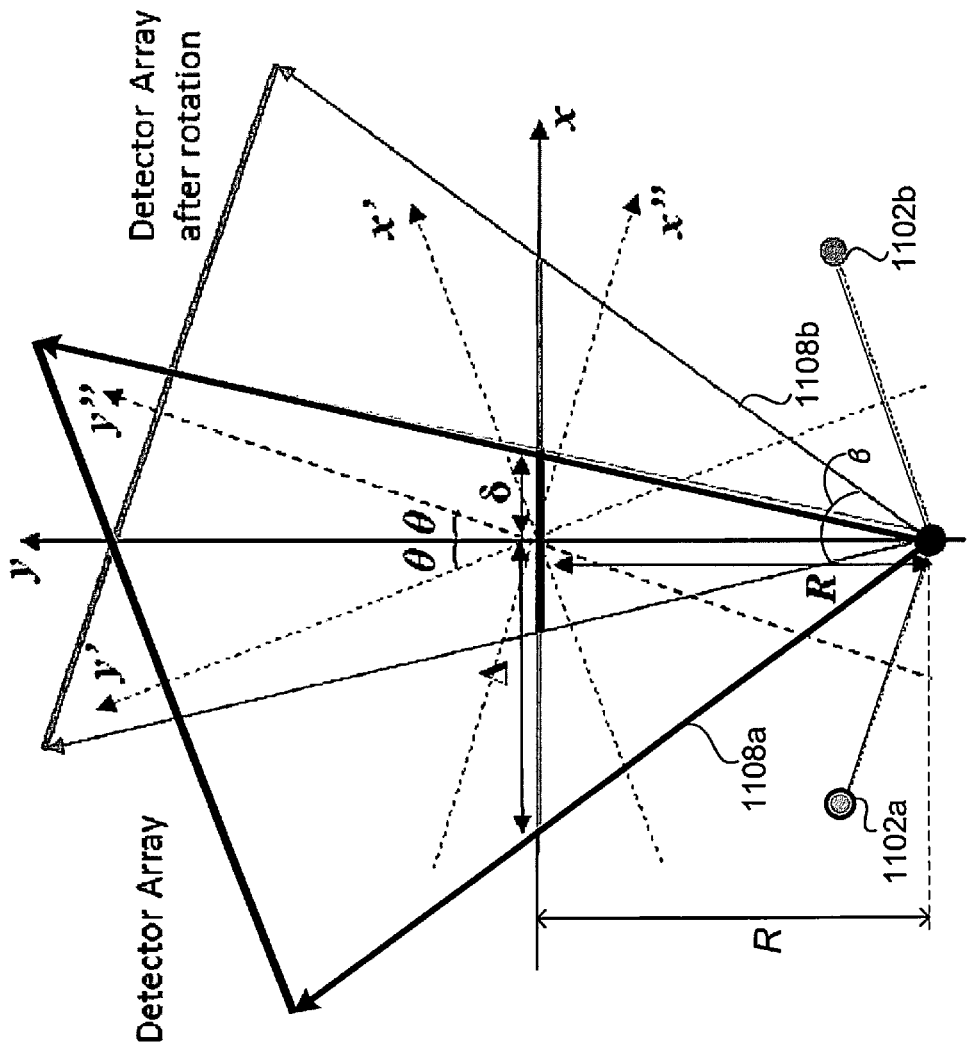
FIG. 17B is a schematic view of the geometry of an exemplary dual source-dual detector tetrahedron beam computed tomography system with a displaced detector.

Referring to FIGS. 17A and 17B, filtered back projection (FBP) is the most widely used image reconstruction algorithm clinically due to its high computational efficiency. The FBP algorithm requires that the detector length covers the entire width of the patient to avoid truncation artifacts. In one dual source-dual detector configuration, all four projections acquired at each gantry angle are transversely truncated. The transverse truncation is similar to the truncation that results from offsetting the FPI during a CBCT scan. To avoid data truncation artifacts, a pre-convolution weighting method may be used. A two-dimensional (2D) reconstruction geometry is shown in FIGS. 17A and 17B.

The equispatial weighting function is given by equation 5:

$$w(t, \beta) = \begin{cases} 1 & t < -\delta \\ \frac{1}{2}\left(\sin\frac{\pi\tan^{-1}(t/R)}{2\tan^{-1}(\delta/R)}\right) + 1, & -\delta \le t \le \delta \\ 0 & t > \delta \end{cases} \quad (5)$$

where t is the position of the detector along the x-axis, β is the projection angle, R is the source to the isocenter distance, and δ is the range of the displaced detector array.

In one embodiment of the dual-source dual-detector TBCT system 1100, the source array 1102 is displaced from the central axis instead of the detector array 1104. However, displacing the source array 1102 is equivalent to displacing the detector array 1104 if the axis running from the source to the isocenter is considered as the central axis. As shown in FIG. 17B, source the first and second source arrays 1102a, 1102b can be displaced to the center by rotating the x'-y' and x"-y" reference frames by angles of −θ and θ, respectively. The projection data is then interpolated onto a virtual detector lying along the x-axis as shown in FIG. 17B. Once the data is scaled onto the x-axis, the data may be used to reconstruct the image.

As shown in FIG. 17B, the projections from the two sets only overlap in the region from −δ to +δ. The weighing function is defined as in equation 6:

$$w_{s1}(x,\beta)=w(x,\beta), w_{s2}(x,\beta)=1-w(x,\beta), \quad (6)$$

which are then applied to the two projection subimages ($I_1$, $I_2$) acquired by the first and second source arrays 1102a, 1102b in order to form a combined projection image. This combined projection (I) image is determined by $$I=w_{s1}I_1+w_{s2}I_2 \quad (7)$$

Figure 18:
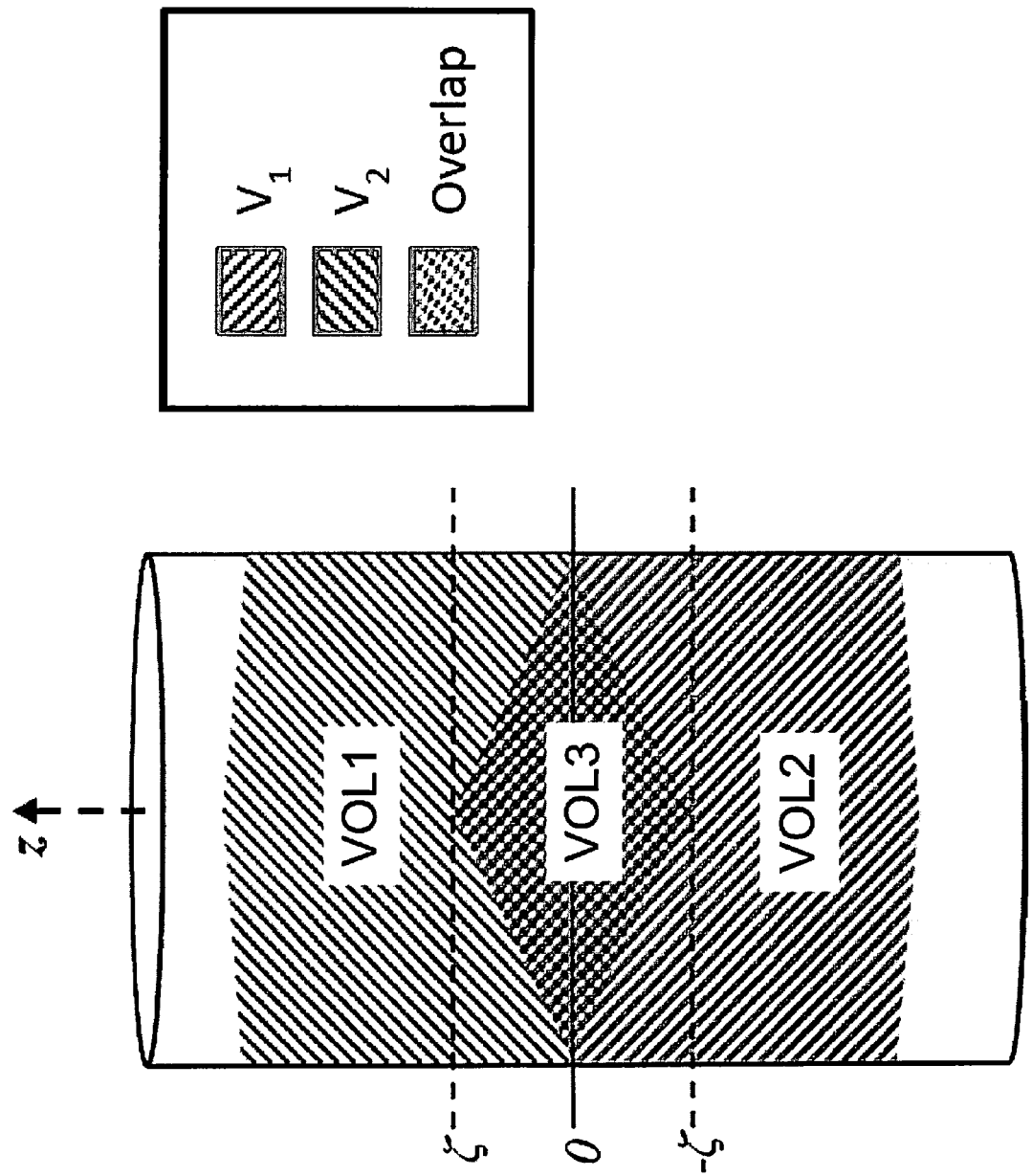
FIG. 18 is a schematic view of two reconstructed subvolumes and the region where the two subvolumes overlap based on an exemplary dual source-dual detector TBCT system.

Referring to FIG. 18, for the dual-source dual-detector system 1100, two sub-images V1 and V2 are acquired by each of the detector arrays 1104a, 1104b. V1 and V2 are overlapped within VOL3. The full reconstruction volume, V, is formed by taking a weighted sum of the two sub-volumes and is defined by equation 8:

$$V=w_1V_1+w_2V_2 \quad (8)$$

where w1 and w2 are the weights of voxel for V1 and V2. The weighting is applied along the z-axis to those voxels in each subvolume where overlap occurs.

Figure 19A:
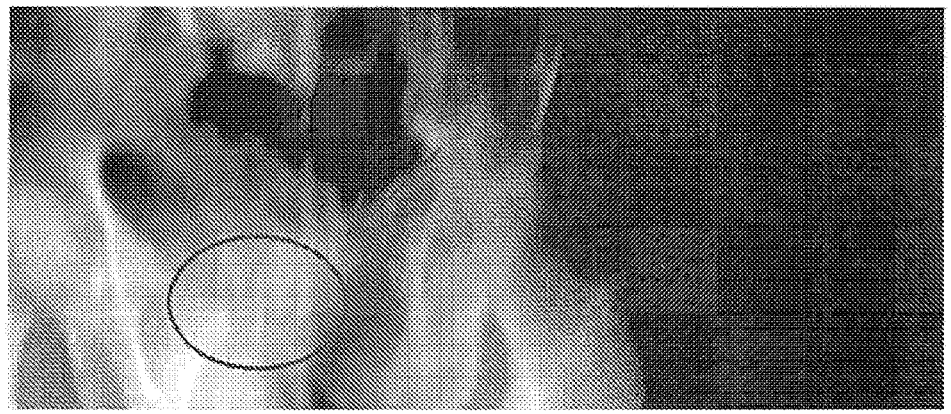
FIG. 19A-19C are simulated radiographic views of a prostate patient with projections shifted to focus the image at different y-axis positions.
Figure 19B:
Figure 19C:
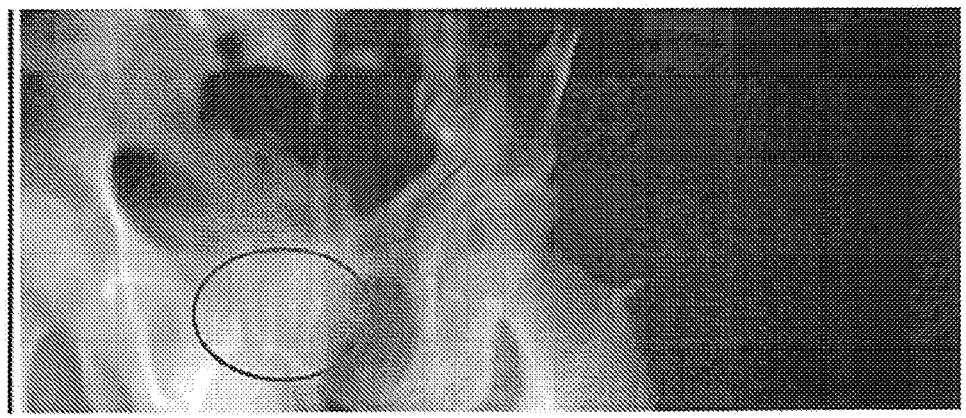

FIG. 19 shows simulated (not actual) reconstructed TBCT radiographic images shifted to sharpen the focus at three different y-axis positions that were determined using equation 3. A detector pixel size of approximately 1.5 mm may be used to generate the projection data, but other detector pixel sizes may be used. In an ideal system with a point focus size, a maximum image resolution at the isocenter of approximately 0.8 mm is provided. The image resolution may be slightly lower due to the focus spot size.

Figure 20:
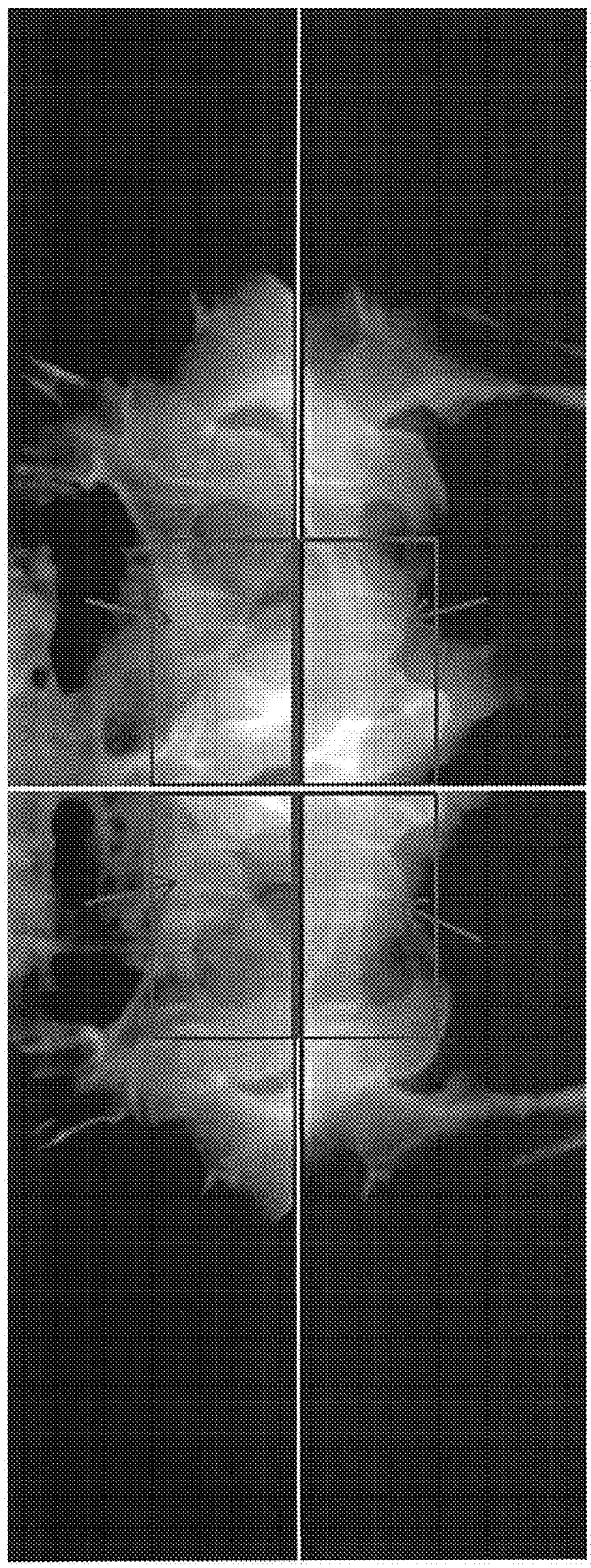
FIG. 20 are simulated projection images generated for each of the four detector array-source array pairs.

Each of the source and detector array pairs (1102a/1104a, 1102a/1104b, 1102b/1104a, and 1102b/1104b) generates a projection image. With two source arrays 1102a, 1102b and two detector arrays 1104a, 1104b, a total of four projection images are generated. Each of the projection images is a view of the object 28 from different angles. FIG. 20 shows four simulated (not actual) projection images produced for each of the source array-detector array pairs. Each detector array 1104a and 1104b provides the two images that make up one of the rows of images seen in FIG. 20. Since these two images would be collected at the same time at different viewing angles, they might be used to create stereoscopic images. Two stereoscopic images that correspond to the two detector arrays 1104a, 1104b could then be produced. In FIG. 20, fiducial markets located around the isocenter could be visualized in all four images. In some examples, the images are off-center because of the geometry of the system. The system 1100 with the dimensions shown in FIG. 5A could provide a 10-15 cm stereoscopic FOV at the central axis, which is marked in the frame of FIGS. 16B and 16C. The dimensions in FIG. 16A are an example. The actual stereoscopic FOV depends on the actual model and vendors of LINACs.

Figure 21:
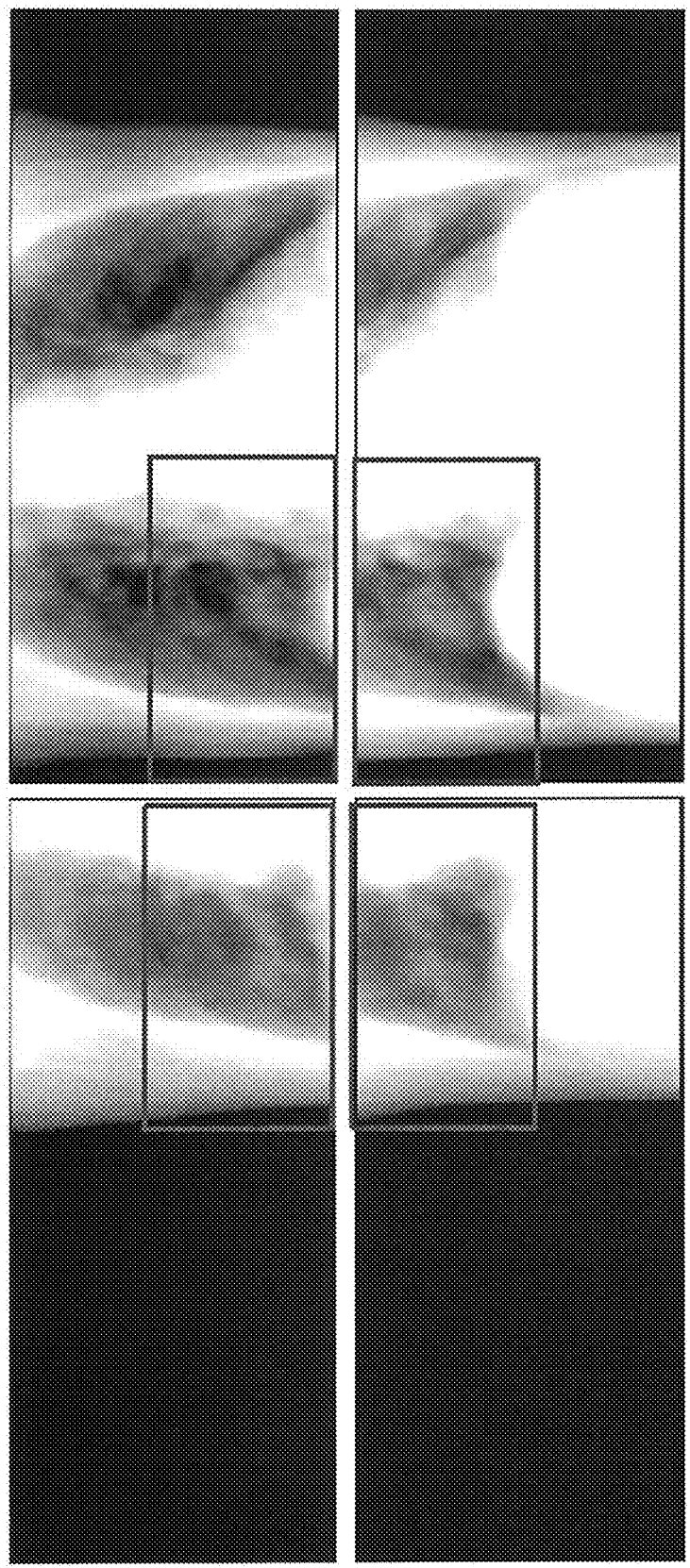
FIG. 21 are simulated projection images generated for each of the four detector array-source array pairs.

Respiratory motion tracking can be a major application of stereoscopic imaging in IGRT. FIG. 21 shows simulated (not actual) projection images of a lung patient from each of the source array-detector array pairs. The object 28 (tumor) could be visualized at the base of the right lung in each projection. As shown, the full motion path of the tumor would be in all four views. Therefore, the dual source-dual detector TBCT system 1100 is able to provide real-time stereoscopic imaging. In some examples, the images may be used for 4D and respiratory-gated lung treatments.

Advanced radiation treatment techniques, such as online and offline adaptive radiotherapy demand high quality online volumetric images. Dose calculation and deformable image registration are important tools for adaptive radiotherapy, and the accuracy of both dose calculation and deformable image registration relies on the quality of the images. CBCT provides neither sufficient contrast for deformable image registration nor accurate CT numbers for dose calculation to produce reliable results. The dual source dual detector TBCT system 1100 provides reconstructed images with image quality that is superior to that provided by CBCT and comparable to the image quality provided by diagnostic CT images.

Gated and 4D radiation treatment techniques for a target with respiratory motion have been proposed and developed, but application of these techniques in clinics is very limited, largely due to the lack of capacity to track the tumor in real-time. Electromagnetic tracking is an invasive procedure that requires the inclusion of additional equipment in the treatment room. The stereoscopic imaging function of the dual source-dual detector TBCT system 1100 is a dramatic improvement for monitoring target motion. The dual source-dual detector TBCT system 1100 tracks motion without requiring the implantation of fiducial markers during treatment. With 4 view angles, the dual source—dual detector TBCT system 1100 achieves 20 frames per second during stereoscopic imaging.

Although a detector grid can reject scatter photons for 2D detectors, it also partially blocks primary photons. Radiography with the TBCT geometry can reject scattered photons without blocking primary photons similarly to a slot-scan system. Hence the radiation exposure of radiographic imaging for TBCT is lower than that of regular radiography. In addition, because of the higher detector DQE and scatter rejection, radiation exposure due to TBCT scans will be similar to that of helical scanners and will be lower than that of CBCT.

Due to the elimination of the additional kV imaging structure, radiation treatment machines would have larger clearance than current systems that employ CBCT. Because of the weight of the x-ray tubes and of the necessity for strict tolerances on the geometry, the supporting structure for the EPID and x-ray tubes would need to be reinforced.

Figure 22:
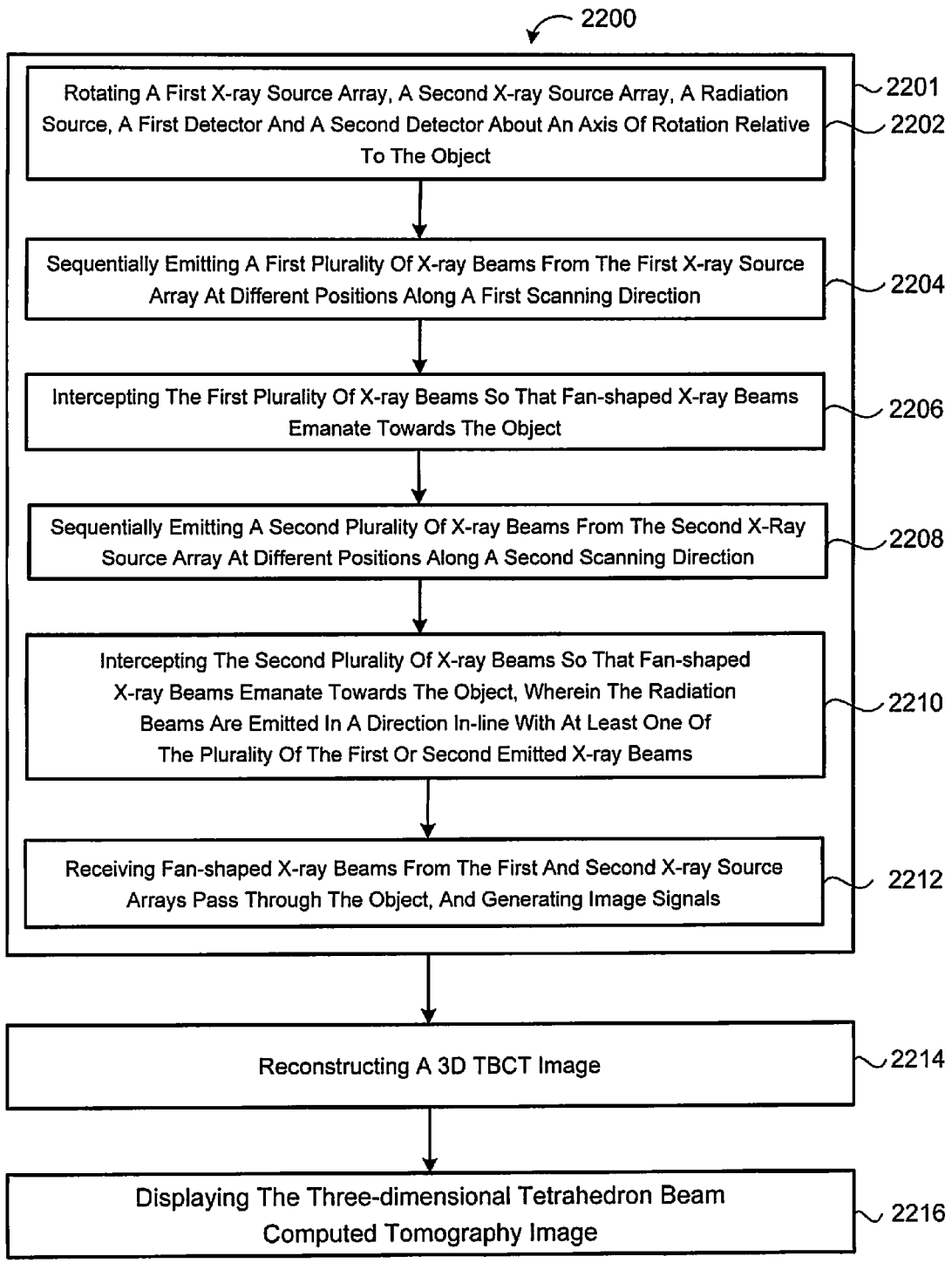
FIG. 22 is a schematic view of an exemplary arrangement of forming an image of an object being exposed to radiation therapy.

FIG. 22 provides a dual-source dual-detection method 2200 of forming an image of an object 28 being exposed to radiation therapy. The method 2200 includes generating 2201 image signals by rotating 2202 a first x-ray source array 1102*a*, a second x-ray source array 1102*b*, a therapy radiation source 1004, a first detector array 1104*a* and a second detector array 1104*b* about an axis of rotation relative to the object 28. The therapy radiation source 1004 is positioned between the first and second detectors 1104*a*, 1104*b* and emits treatment beam 1008. Generating 2201 image signals further includes emitting 2204 (e.g., sequentially) a first plurality of x-ray beams 1108*aa*-1108*an* from the first x-ray source array 1102*a* at different positions along a first scanning direction and intercepting 2206 the first plurality of x-ray beams 1108*aa*-1108*an* so that fan-shaped x-ray beams emanate towards the object 28. Generating 2201 image signals also includes emitting 2208 (e.g., sequentially) a second plurality of x-ray beams 1108*ba*-1108*bn* from the second x-ray source array 1102*b* at different positions along a second scanning direction, and intercepting 2210 the second plurality of x-ray beams 1108*ba*-1108*bn* so that fan-shaped x-ray beams emanate towards the object 28. The treatment beam 1008 is emitted in a direction in-line with at least one of the plurality of the first or second emitted x-ray beams 1108*a*, 1108*b*.

Generating 2201 image signals includes receiving 2212 at the first detector 1104*a* a first portion of the plurality of fan-shaped x-ray beams 1108*aa*-1108*an*, from the first x-ray source array 1102*a* after the x-ray beams pass through the object 28 and a first portion of the plurality of fan-shaped x-ray beams 1108*ba*-1108*bn* from the second x-ray source array 1102*b* after the x-ray beams pass through the object 28. The first detector 1104*a* generates a first imaging signal for each of the received first portion of the plurality of fan-shaped x-ray beams from the first x-ray source array 1102*a* and the received first portion of the plurality of fan-shaped x-ray beams from the second x-ray source array 1102*b*.

Generating 2201 image signals also includes receiving 2212, at the second detector 1104*b*, a second portion of the plurality of fan-shaped x-ray beams 1108*aa*-1108*an* from the first x-ray source 1102*a* after the x-ray beams pass through the object 28 and a second portion of the plurality of fan-shaped x-ray beams 1108*ba*-1108*bn* from the second x-ray source 1102*b* after the x-ray beams pass through the object 28. The second detector 1104*b* generates a second imaging signal for each of the received second portion of the plurality of fan-shaped x-ray beams from the first x-ray source 1102*a* and the received second portion of the plurality of fan-shaped x-ray beams from the second x-ray source 1102*b*.

The method 2200 also includes reconstructing a 3D TBCT image 2214 from the first imaging signals (for each first portion of the first plurality of fan-shaped x-ray beams 1108*a* from the first x-ray source 1102*a* and for each first portion of the first plurality of fan-shaped x-ray beams 1108*b* from the second x-ray source 1102*b*) and the second imaging signals (for each first portion of the second plurality of fan-shaped x-ray beams 1108*a* from the first x-ray source 1102*a* and for each first portion of the second plurality of fan-shaped x-ray beams 1108*b* from the second x-ray source 1102*b*). The rotation of the first x-ray source array 1102*a*, the second x-ray source array 1102*b*, the first detector 1104*a* and the second detector 1104*b* about the axis of rotation results in multiple imaging signals being reconstructed to generate a three-dimensional tetrahedron beam computed tomography image therefrom. The method 2200 also includes displaying 2216 the three-dimensional tetrahedron beam computed tomography image.

In some implementations, the method 2200 includes generating 2201 image signals at least 360 times within a full rotation (360 degrees), i.e., generating image signals at every angle within the full rotation of the gantry. In some examples, generating 2201 image signals occurs at least 1000 times within a full rotation of the gantry, i.e., every 0.36 angles. Other examples are also possible.

In some examples, the method 2200 includes reconstructing stereoscopic images. Specifically, the method 2200 includes reconstructing a stereoscopic (two-dimensional) image from image signals (a first, second, third, and fourth image signals) at one gantry angle (i.e., at one position of the gantry). The first image signal for a received first plurality of fan-shaped kilovolt x-ray beams is from the first x-ray source array 1102*a* and the second image signal for the received second plurality of fan-shaped kilovolt x-ray beams is from the second x-ray source array 1102*b*. The third image signal for the received third plurality of fan-shaped kilovolt x-ray beams is from the first x-ray source 1102*a* and the fourth imaging signal for the received fourth plurality of fan-shaped kilovolt x-ray beams is from the second x-ray source 1102*b*). This means a stereoscopic image may be reconstructed when the method 2202 receives the first, second, third, and fourth image signals from the first and second detectors 1104*a*, 1104*b*. In contrast, a three dimensional image can be reconstructed from a plurality of first, second, third, and fourth image signals, each of the plurality of first, second, third, and fourth image signals is generated when the gantry is at a different position of rotation. In particular, for 3D imaging, the plurality of first, second, third, and fourth image signals includes a first, second, third, and fourth image signal generated at a first angle (position) of the gantry; a first, second, third, and fourth image signal generated at a second angle (position) of the gantry; a first, second, third, and fourth image signal generated at a third angle (position) of the gantry; etc.

In some examples, the megavoltage radiotherapy system 1000 includes an electronic portal imaging device 1010 in communication with the computer, where the first and second x-ray sources 1102*a*, 1102*b* are positioned on either side of the electronic portal imaging device 1010 or where the first and second detectors 1104*a*, 1104*b* are positioned on either side of the electronic portal imaging device 1010. In some examples, the first and second x-ray source arrays 1102*a*,

1102*b* are orthogonal to the first and second detectors 1104*a*, 1104*b*. Each of the source array 1102*a*, 1102*b* and detector array 1104*a*, 1104*b* pairs may generate a projection image. In some examples, one of the plurality of emitted x-ray beams 1108 is substantially parallel to at least one of the emitted radiation beams 1008.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A radiation treatment and imaging system for emitting a radiation treatment beam and X-ray imaging beams towards an object, the radiation treatment and imaging system comprising:
 a first x-ray source array emitting a first plurality of x-ray beams at different positions along a scanning direction;
 a first collimator positioned to intercept the first plurality of x-ray beams emitted by the first x-ray source array so that a first plurality of fan-shaped x-ray beams emanate from the first collimator towards the object;
 a first detector positioned to receive a first portion of the first plurality of x-ray beams emitted by the first x-ray source array and generating a first imaging signal based on the first portion of the first plurality of x-ray beams;
 a second detector positioned to receive a second portion of the first plurality of x-ray beams emitted by the first x-ray source array and generating a second imaging signal based on the second portion of the first plurality of x-ray beams;
 a linear accelerator delivering a radiation beam from a megavolt radiation source to the object, the megavolt radiation source positioned between the first and second detectors and emitting treatment radiation beams in a direction in-line with the first plurality of x-ray beams;
 a data processing device in communication with the first and second detectors, the data processing device receiving the first and second imaging signals, wherein the first x-ray source array, the first and second detectors, and the linear accelerator rotate about a rotation axis causing the data processing device to receive more than one first and second imaging signals, the data processing device reconstructing the received imaging signals generating a three-dimensional tetrahedron beam computed tomography image therefrom; and
 a display connected to the data processing device and displaying the three-dimensional tetrahedron beam computed tomography image.

2. The system of claim 1, wherein the first x-ray source array sequentially emits the first plurality of x-ray beams.

3. The system of claim 1, wherein the first x-ray source array is orthogonal to the first and second detectors.

4. The system of claim 1, further comprising:
 a second x-ray source array emitting a second plurality of x-ray beams at different positions along a scanning direction; and
 a second collimator positioned to intercept the second plurality of x-ray beams emitted by the second x-ray source array so that a second plurality of fan-shaped x-ray beams emanate from the second collimator towards the object;
 wherein the first detector receives a first portion of the second plurality of x-ray beams emitted by the second x-ray source array, and the generated first imaging signal is based on the first portion of the first plurality of x-ray beams and the first portion of the second plurality of x-ray beams; and
 wherein the second detector receiving a second portion of the second plurality of x-ray beams emitted by the second x-ray source array, the generated second imaging signal based on the second portion of the first plurality of x-ray beams and the second portion of the second plurality of x-ray beams.

5. The system of claim 4, wherein the second x-ray source array sequentially emits the second plurality of x-ray beams.

6. The system of claim 4, wherein the first and second x-ray source arrays are orthogonal to the first and second detectors.

7. The system of claim 1, wherein the linear accelerator comprises an electronic portal imaging device in communication with the data processing device, and the first and second x-ray source arrays are positioned on either side of the electronic portal imaging device.

8. A radiation treatment and imaging system for emitting a radiation beam and X-ray beams towards an object, the radiation treatment and imaging system comprising:
 a linear accelerator that delivers a radiation beam from a megavolt radiation source to the object;

a tetrahedron beam computed tomography system for imaging the object as the object is exposed to radiation beams, the tetrahedron beam computed system comprising:
- a first x-ray source array that emits first and third pluralities of kilovolt x-ray beams at different positions along a first scanning direction;
- a first collimator that intercepts the first and third pluralities of kV x-ray beams so that fan-shaped kV x-ray beams emanate from the first collimator towards the object;
- a second x-ray source array that emits second and fourth pluralities of kilovolt x-ray beams at different positions along a second scanning direction;
- a second collimator that intercepts the second and fourth pluralities of kilovolt x-ray beams so that fan-shaped kilovolt x-ray beams emanate from the second collimator towards the object;
- a first detector positioned to receive 1) the first plurality of fan-shaped kilovolt x-ray beams from the first x-ray source array and 2) the second plurality of fan-shaped kilovolt x-ray beams from the second x-ray source array after they pass through the object, the first detector generating first and second imaging signals for each of the received first and second pluralities of fan-shaped kilovolt x-ray beams from the first and second kilovolt x-ray source arrays, respectively;
- a second detector positioned to receive 1) the third plurality of fan-shaped kilovolt x-ray beams from the first x-ray source array and 2) the fourth plurality of fan-shaped kilovolt x-ray beams from the second x-ray source array after they pass through the object, the second detector generating third and fourth imaging signals for each of the received third and fourth pluralities of fan-shaped kilovolt x-ray beams from the first and second x-ray source arrays, respectively;
- a computer connected to the first and the second detectors so as to receive 1) the first imaging signals for each of the first plurality of fan-shaped x-ray beams received by the first detector and 2) the second imaging signals for each of the second plurality of fan-shaped kilovolt x-ray beams received by the first detector, 3) the third imaging signals for each of the third plurality of fan-shaped kilovolt x-ray beams received by the second detector, 4) the fourth imaging signals for each of the fourth plurality of fan-shaped kilovolt x-ray beams received by the second detector, wherein the first x-ray source array, the second x-ray source array, the first detector, and second detector rotate about a rotation axis so as to rotate about the object so that multiple imaging signals are reconstructed by the computer to generate a three-dimensional tetrahedron beam computed tomography image therefrom; and
- a display connected to the computer and displaying the three-dimensional tetrahedron beam computed tomography image;
- wherein the megavolt radiation source is positioned between the first and second detectors and emits treatment radiation beams in a direction in-line with the imaging kilovolt x-ray beams.

9. The system of claim 8, wherein the linear accelerator comprises an electronic portal imaging device in communication with the computer, and the first and second x-ray source arrays are positioned on either side of the electronic portal imaging device.

10. The system of claim 8, wherein the first and second x-ray source arrays are orthogonal to the first and second detectors.

11. The system of claim 8, wherein each source array and detector pair generates a projection image.

12. The system of claim 8, wherein the first and second x-ray source arrays comprise an array of kV x-ray sources and the megavolt radiation source generates a beam of x-rays having an energy up to 25 MeV.

13. The system of claim 8, wherein the signals of the first, the second, the third and the fourth plurality of kilovolt x-ray beams generate first, second, third and fourth two dimensional projection images.

14. The system of claim 8, wherein the computer determines a location of a feature using at least two projection images.

15. The system of claim 8, wherein the first, second, third and fourth pluralities of emitted kilovolt x-ray beams share a central axis with the radiation beam.

16. A method of forming an image of an object being exposed to radiation therapy, the method comprising:
- positioning a therapy radiation source between a first detector and a second detector;
- emitting a first plurality of kilovolt x-ray beams from a first x-ray source array;
- intercepting the first plurality of kilovolt x-ray beams so that fan-shaped x-ray beams emanate towards the object;
- emitting a second plurality of kilovolt x-ray beams from a second x-ray source array at different positions;
- intercepting the second plurality of kilovolt x-ray beams so that fan-shaped x-ray beams emanate towards the object;
- emitting a third plurality of kilovolt x-ray beams from the first x-ray source array;
- intercepting the third plurality of kilovolt x-ray beams so that fan-shaped kilovolt x-ray beams emanate towards the object;
- emitting a fourth plurality of kilovolt x-ray beams from the second x-ray source array;
- intercepting the fourth plurality of kilovolt x-ray beams so that fan-shaped kilovolt x-ray beams emanate towards the object;
- receiving at the first detector, 1) a first plurality of fan-shaped kilovolt x-ray beams from the first x-ray source array after the x-ray beams pass through the object and 2) a second plurality of fan-shaped kilovolt x-ray beams from the second x-ray source array after the x-ray beams pass through the object, wherein the first detector generates a first imaging signal for the received first plurality of fan-shaped kilovolt x-ray beams from the first x-ray source array and a second imaging signal for the received second plurality of fan-shaped kilovolt x-ray beams from the second x-ray source array;
- receiving at the second detector, 1) a third plurality of fan-shaped kilovolt x-ray beams from the first x-ray source after the x-ray beams pass through the object and 2) a fourth plurality of fan-shaped kilovolt x-ray beams from the second x-ray source array after the x-ray beams pass through the object, wherein the second detector generates a third imaging signal of the received third plurality of fan-shaped kilovolt x-ray beams from the first x-ray source array and a fourth imaging signal from the received fourth plurality of fan-shaped kilovolt x-ray beams from the second x-ray source array;
- determining a stereoscopic image based on the 1) the first imaging signals for each of the first plurality of fan-shaped kilovolt x-ray beams from the first x-ray source array and the second imaging signals for each of the second plurality of fan-shaped kilovolt x-ray beams from the second x-ray source array and 2) the third imaging signals for each of the third plurality of fan-shaped kilovolt x-ray beams from the first x-ray source array and the fourth imaging signals for each of the fourth plurality of fan-shaped kilovolt x-ray beams from the second x-ray source array; and displaying the stereoscopic image.

17. The method of claim 16, wherein the therapy radiation source comprises an electronic portal imaging device, the first and second x-ray source arrays positioned on either side of the electronic portal imaging device.

18. The method of claim 16, wherein the first and second x-ray source arrays are orthogonal to the first and second detectors.

19. The method of claim 16, wherein each source array and detector pair generates a projection image.

20. The method of claim 16, wherein the first and second x-ray source arrays comprise a kilovolt x-ray source and the therapy radiation source generates a beam of x-rays having an energy up to 25 MeV.

21. The method of claim 16, wherein the first, second, third and fourth pluralities of emitted kilovolt x-ray beams share a central axis with a radiation beam from the therapy radiation source.

22. The method of claim 16, wherein none, one, or both of the first and third pluralities of kV x-ray beams are sequentially emitted from the first x-ray source array and none, one, or both of the second and fourth pluralities of kV x-ray beams are sequentially emitted from the second x-ray source array.

23. A method of forming a three-dimensional tetrahedron beam computed tomography image of an object being exposed to radiation therapy, the method comprising:

rotating a first x-ray source array, a second x-ray source array, a therapy radiation source, a first detector and a second detector about an axis of rotation relative to the object, wherein the therapy radiation source is positioned between the first and second detectors and emitting radiation beams;

emitting a first plurality of kilovolt x-ray beams from the first x-ray source array at different positions;

intercepting the first plurality of kilovolt x-ray beams so that fan-shaped x-ray beams emanate towards the object;

emitting a second plurality of kilovolt x-ray beams from the second x-ray source array at different positions;

intercepting the second plurality of kilovolt x-ray beams so that fan-shaped x-ray beams emanate towards the object;

emitting a third plurality of kilovolt x-ray beams from the first x-ray source array at different positions;

intercepting the third plurality of kilovolt x-ray beams so that fan-shaped kilovolt x-ray beams emanate towards the object;

emitting a fourth plurality of kilovolt x-ray beams from the second x-ray source array at different positions;

intercepting the fourth plurality of kilovolt x-ray beams so that fan-shaped kilovolt x-ray beams emanate towards the object;

receiving at the first detector, 1) a first plurality of fan-shaped kilovolt x-ray beams from the first x-ray source array after the x-ray beams pass through the object and 2) a second plurality of fan-shaped kilovolt x-ray beams from the second x-ray source array after the x-ray beams pass through the object, wherein the first detector generates a first imaging signal for the received first plurality of fan-shaped kilovolt x-ray beams from the first x-ray source array and a second imaging signal for the received second plurality of fan-shaped kilovolt x-ray beams from the second x-ray source array;

receiving at the second detector, 1) a third plurality of fan-shaped kilovolt x-ray beams from the first x-ray source after the x-ray beams pass through the object and 2) a fourth plurality of fan-shaped kilovolt x-ray beams from the second x-ray source and after the x-ray beams pass through the object, wherein the second detector generates a third imaging signal of the received third plurality of fan-shaped kilovolt x-ray beams from the first x-ray source array and a fourth imaging signal from the received fourth plurality of fan-shaped kilovolt x-ray beams from the second x-ray source array;

determining a three-dimensional tetrahedron beam computed tomography image based on the 1) the first imaging signals for each of the first plurality of fan-shaped kilovolt x-ray beams from the first x-ray source and the second imaging signals for each of the second plurality of fan-shaped kilovolt x-ray beams from the second x-ray source and 2) the third imaging signals for each of the third plurality of fan-shaped kilovolt x-ray beams from the first x-ray source and the fourth imaging signals for each of the fourth plurality of fan-shaped kilovolt x-ray beams from the second x-ray source, wherein rotation of the first x-ray source array, the second x-ray source array, the first detector and the second detector about the axis of rotation generates multiple imaging signals used to reconstruct the three-dimensional tetrahedron beam computed tomography image therefrom; and displaying the three-dimensional tetrahedron beam computed tomography image.

* * * * *